US010468142B1

(12) United States Patent
Abou Shousha et al.

(10) Patent No.: US 10,468,142 B1
(45) Date of Patent: Nov. 5, 2019

(54) ARTIFICIAL INTELLIGENCE-BASED SYSTEM AND METHODS FOR CORNEAL DIAGNOSIS

(71) Applicant: University of Miami, Miami, FL (US)

(72) Inventors: Mohamed Abou Shousha, Pembroke Pines, FL (US); Amr Saad Mohamed Elsawy, South Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 16/047,944

(22) Filed: Jul. 27, 2018

(51) Int. Cl.
| *G16H 50/50* | (2018.01) |
| *A61B 3/00* | (2006.01) |
| *A61B 3/107* | (2006.01) |
| *G06T 7/00* | (2017.01) |
| *G16H 50/20* | (2018.01) |
| *A61B 3/10* | (2006.01) |
| *A61B 3/117* | (2006.01) |
| *A61B 3/14* | (2006.01) |

(52) U.S. Cl.
CPC ........... *G16H 50/50* (2018.01); *A61B 3/0025* (2013.01); *A61B 3/102* (2013.01); *A61B 3/1005* (2013.01); *A61B 3/107* (2013.01); *A61B 3/117* (2013.01); *A61B 3/14* (2013.01); *G06T 7/0012* (2013.01); *G16H 50/20* (2018.01); *G06T 2207/10024* (2013.01); *G06T 2207/10101* (2013.01); *G06T 2207/20076* (2013.01); *G06T 2207/20081* (2013.01); *G06T 2207/30041* (2013.01)

(58) Field of Classification Search
CPC ...... G16H 50/50; G16H 50/20; A61B 3/0025; A61B 3/1005; A61B 3/117; A61B 3/107; A61B 3/102; A61B 3/14; G06T 7/0012; G06T 2207/10024; G06T 2207/20081; G06T 2207/30041; G06T 2207/10101; G06T 2207/20076
See application file for complete search history.

(56) References Cited

U.S. PATENT DOCUMENTS

| 10,121,059 | B2 * | 11/2018 | Yoo | G06K 9/00228 |
| 2005/0225724 | A1 * | 10/2005 | Klyce | A61B 3/107 351/212 |
| 2006/0210122 | A1 * | 9/2006 | Cleveland | A61B 3/107 382/117 |
| 2013/0128222 | A1 * | 5/2013 | Huang | A61B 3/1005 351/206 |
| 2017/0357879 | A1 * | 12/2017 | Odaibo | G06K 9/6256 |

* cited by examiner

*Primary Examiner* — John W Lee
(74) *Attorney, Agent, or Firm* — Pillsbury Winthrop Shaw Pittman, LLP

(57) ABSTRACT

A method of predicting a disease or condition of a cornea or an anterior segment of an eye includes inputting input data into an AI model, processing the input data, and generating a set of scores and outputting a prediction. The input data may be representative of a cornea or anterior segment of an eye. Processing the input data may include processing the data through the plurality of convolutional layers, the fully connected layer, and the output layer. Each score of the set of scores may be generated by a corresponding node in the output layer. The output prediction may be related to the cornea or anterior segment of the eye represented by the input data processed through the AI model. The prediction may be determined by at least one score of the set of scores.

28 Claims, 27 Drawing Sheets

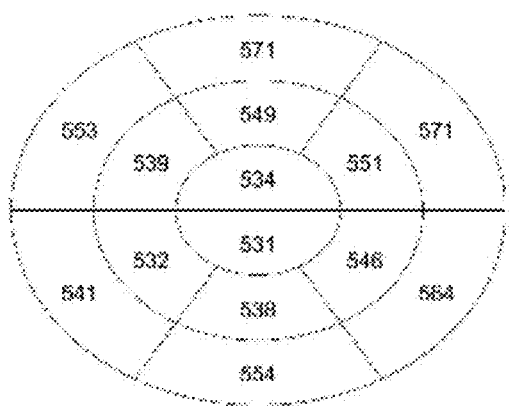
FIG. 2C
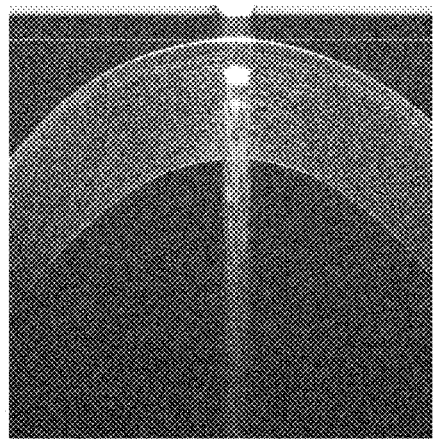 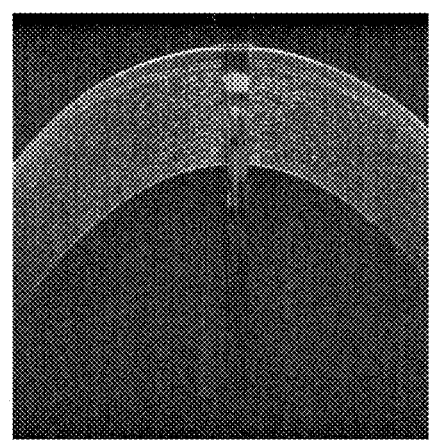
FIG. 3A  FIG. 3B

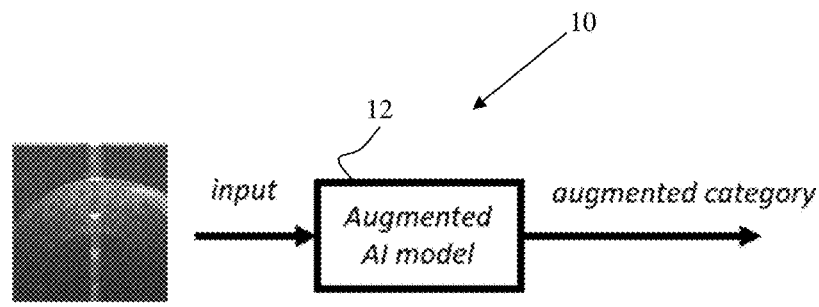
FIG. 19A
| disease | severity | risk | action | treatment | Category |
|---------|----------|------|--------|-----------|----------|
| ... | ... | ... | ... | ... | ... |
| $d_k$ | $s_k$ | $r_k$ | $a_k$ | $t_k$ | $c_k$ |
| ... | ... | ... | ... | ... | ... |
| | | | | | |
FIG. 19B
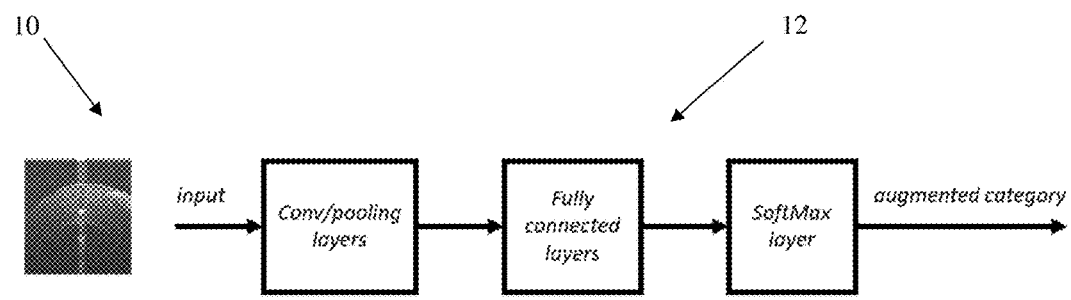
FIG. 19C

ARTIFICIAL INTELLIGENCE-BASED SYSTEM AND METHODS FOR CORNEAL DIAGNOSIS

STATEMENT OF GOVERNMENT SUPPORT

This invention was made with government support under Grant No. K23EY026118 awarded by the National Institute of Health. The Government has certain rights in the invention.

TECHNOLOGY FIELD

The present disclosure relates to artificial intelligence based systems and methods for diagnosis, evaluation, and analysis of corneal diseases or conditions and treatments thereof. The present disclosure further relates to deep learning and neural network architectures for deployment of artificial intelligence based systems and methods for diagnosis, evaluation, and analysis of corneal diseases or conditions and treatments thereof.

BACKGROUND

There are many conditions that affect the anterior segment of the eye. Some common conditions, for example, include aqueous deficiency and evaporative dry eye syndrome (DES), corneal ectasia, corneal limbal stem cell deficiency, keratoplasty graft rejection episode and failure, and Fuchs' dystrophy. However, conditions such as these are difficult to diagnose and treat.

Dry Eye Syndrome: Dry eye syndrome (DES) is a worldwide public health problem. In the United States alone, an estimated 25 million patients suffer from DES. DES adversely affects vision and causes constant symptoms of dryness, eye irritation, and foreign body sensation and thus negatively impacts patients' quality of life. Severe DES can lead to corneal melting compromising the integrity of the eye and can cause blindness. DES can be classified into aqueous deficiency DES or evaporative DES. In aqueous deficiency DES, there is deficiency in the quantity of tears secreted by the lacrimal glands. Whereas, in evaporative dry eye, which is caused by meibomian gland dysfunction (MGD), the problem lies in deficiency in the lipid layer of the tear film leading to excessive evaporation of the tears. The diagnosis and treatment of DES has become a challenge. Major research is directed at finding new remedies for DES but those efforts are limited by the fact that there is no gold standard for the diagnosis of DES. Available diagnostic tests lack standardization and usually are not representative of patient symptoms, in addition to other limitations.

The medical literature has shown poor association between current dry eye test and patient symptoms. Additionally, the current tests are poorly standardized tests as they are affected by factors that are difficult to control. For example, tear breakup time is affected by temperature and humidity of the examination room. Moreover, reflex lacrimation as the patient keeps his or her eyes open to obtain measurements can invalidate obtained measurements. The Schirmer test (in which paper strips are inserted into the eye to measure moisture production) is invasive and unpleasant to the patient. Further, hanging filter paper from a patient's eyes could result in reflex tearing that can affect obtained measurements. Fluorescein or other vital stains of the ocular surface are examples of tests that detect the injurious effect of DES on the ocular surface epithelium; however, results of those tests are identified using a slit lamp with magnification of only up to 16×. Such accuracy might be enough to diagnose moderate to severe dry eye, but certainly would not be enough to detect mild cases or monitor response to treatment. Indeed, the discrepancy between signs and symptoms of dry eye patients most likely stems from a lack of accuracy. Corneal nerves are sensitive enough to detect microscopic injuries to the ocular surface, but the available tests are not sensitive enough to visualize that injury or quantify it. Another limitation of current clinical techniques is that many are subjectively evaluated. What an examiner would consider mild corneal and conjunctival fluorescein staining, another could consider moderate and vice versa.

Diagnostic modalities have been recently introduced such as confocal microscopy and tear film osmolarity. Using confocal microscopy to diagnose DES is a time-consuming procedure that requires contact with the ocular surface and that makes it difficult to incorporate into everyday clinics and limits its use to research. Furthermore, it can only capture images over a small area of the total cornea. Tear film osmolarity has shown promise as a quantitative method to diagnose DES, but it is also invasive and time consuming. The literature has also shown lack of a cut off tear osmolarity values and a great overlap between normal subjects and DES patients. Until enough data proves otherwise, lubricating a dry eye would be able to improve the health of the ocular surface by providing an alternative to the inadequate natural tears, but does not alter the tear film osmolarity. Thus, looking at the osmolarity might not provide an insight about the response of the patient to treatment.

Corneal ectasia is a progressive disease that adversely affects the structural integrity of the cornea. The weakened cornea bulges, and crippling irregular astigmatism starts to develop. The astigmatism degrades vision and as the disease progresses, scarring of the cornea occurs. Corneal ectasia includes keratoconus, pellucid marginal degeneration, post-refractive surgery ectasia, and other rare diseases such as keratoglobus. Modalities for the treatment of corneal ectasia have been developed, such as corneal collagen cross-linkage that uses ultraviolet (UV) light and Riboflavin to stiffen the cornea and halt the progression of the disease. It is desirable to halt the progression of the disease at a very early stage, before vision is degraded by irregular astigmatism or scarring. Therefore, there is a need for a specific and sensitive sign that can detect those early patients to allow treatment before irreversible corneal damage occurs.

Post-refractive surgery ectasia is a devastating complication of refractive surgery, an elective procedure received by millions of patients in the United States alone. The most common cause of this complication that threatens vision in those patients is performing the refractive surgery on an early ectasia patient who was not detected by the conventional current diagnostic techniques. This highlights the need for a specific and sensitive sign that can be used to detect those early patients to save them from such a devastating complication.

Corneal topography and thickness are among the current diagnostic criteria of ectasia. Their use is complicated by their variations among the general populations. Normal range of corneal thicknesses is wide, and overlapping between normal thin corneas and early ectasia patients complicates the use of this criterion in the diagnosis of early cases of ectasia. Thus, lack of specificity is a significant limitation of using corneal thickening for the diagnosis of the ectasia. Corneal topography use in diagnosis of ectasia shares the same limitations as corneal thinning Irregular astigmatism is seen in normal subjects and in ectasia patients complicating its use to make the diagnosis, especially in mild cases.

Keratoplasty Graft Rejection/Failure and Fuchs' Dystrophy: Keratoplasty, or corneal transplantation, is used to replace a damaged or diseased cornea with a donated corneal tissue graft. About 60,000 corneal transplants are performed every year in the United States alone, it is not uncommon for a graft recipient's body to reject the donated corneal tissue. In fact, it is estimated that 50% of those patients will experience at least one episode of rejection, and 20% of transplants will ultimately fail by the third year, commonly due to the patient's immune system attacking the graft endothelium and destroying it. To preserve the graft and prolong its survival, rejection must be detected and reversed as early as possible. Unfortunately, however, the early stages of rejection are not easily identified. Currently, methods such as slit-lamp examination are used to detect rejection, but this method offers only limited magnification and mild subclinical rejection episodes are often missed. Further, performing endothelial cell count using specular microscopy lacks sufficient reproducibility, sensitivity, and specificity. Finally, measuring the central cornea thickness lack sufficient sensitivity to make it useful in the diagnosis of mild cases, and the wide range of normal corneal thickness complicates it use for diagnosis of mild corneal graft rejection and edema.

Fuchs' dystrophy (or Fuchs' endothelial dystrophy) is a degenerative disease of the corneal endothelium with accumulation of guttae (focal outgrowths) from the endothelial surface of the cornea. Degeneration of the corneal endothelial cells in Fuchs' dystrophy leads to corneal edema and vision loss. Although the disease is most common in people in their 50s and 60s, Fuchs' dystrophy can begin to affect people while in their 30s and 40s, so it is important to accurately identify the condition in its early stages. The same commonly used methods of detecting corneal graft rejection are often used to diagnose Fuchs' dystrophy, but these methods have the same limitations as discussed above. Additionally, there is no cut-off value that can define rejection, failure, or Fuchs' dystrophy. Similarly, using endothelial cell count is equally imprecise, as there is no cut-off value for endothelial cell count. The number of endothelial cells that can maintain a clear cornea is unknown. Further, it has been shown that reliable endothelial cell count is not possible in at least one third of Fuchs' dystrophy patients.

Fuchs' dystrophy is the leading cause of corneal transplantation in the United States, accounting for almost a quarter of all keratoplasties. About 5% of the United States population older than 40 years has Fuchs' dystrophy. This condition is an aging disease and as our population ages, the prevalence of Fuchs' dystrophy is expected to rise even more and is thus expected to impose an even more significant public health problem. Fuchs' dystrophy imposes challenge on eye banking. The confusion between normal subjects and early Fuchs' dystrophy carries the risk of either transplanting patients with early Fuchs' dystrophy corneal grafts or, on the other hand, the unnecessary wasting of corneal tissue. Further, the demand on corneal tissue is growing. The aging of the population, the increased prevalence of Fuchs' dystrophy, and the lowered threshold for endothelial keratoplasty are widening the gap between the demand and the supply. However, developing de novo corneal guttae in corneal grafts has been reported, which is most likely an effect of transplanting undiagnosed Fuchs' dystrophy grafts.

Limbal stem cell deficiency of the cornea is another concern. Limbal stem cells are responsible for repopulating the corneal epithelium. Deficiency in the stem cell of the cornea leads to failure of the epithelium to renew or repair itself. This results in epithelial defects of the cornea that is persistent and resistant to treatment and loss of the corneal clarity leading to blindness. The basal epithelial layer of the cornea is the inner most layer of epithelial cells that is produced by those stem cells and is a precursor of the more superficial layers of the corneal epithelium. The diagnosis of limbal stem cell deficiency (LSCD) is currently done using the slit lamp which uses up to a magnification of only 16× and is unable to visualize the limbal stem cells nor the basal epithelial layer. Confocal microscopy is able to visualize the basal layer of the epithelium but through a very small window (0.4 mm×0.4 mm) and that is not representative of the cornea as a whole. It is also not possible to construct cross-sectional view of those cell layers.

Optical coherence tomography (OCT) is a noninvasive optical signal acquisition and processing method that captures micrometer-resolution, three-dimensional images from within, for example, biological tissue. OCT has proven to be an indispensable tool for imaging the retina and the optic nerve. It has changed the practice of ophthalmology and has become the gold standard for diagnosis and management of diseases with significant morbidity and prevalence such as age-related macular degeneration and glaucoma. Nevertheless, OCT has not yet achieved such a role in anterior segment in general and cornea imaging in particular. This is most likely due to the lack of standardized clinical applications for the device in imaging the anterior segment and cornea.

It is therefore desirable to provide improved systems and methods for diagnosing corneal conditions such as dry eye syndrome, corneal ectasia, keratoplasty rejection and failure, and Fuchs' dystrophy. It is further desirable that these improved systems and methods be usable with current and future imaging devices such as OCT systems, or any other imaging device or system capable of providing high-resolution images of the eye and in particular the cornea, for identifying and monitoring corneal conditions.

SUMMARY

In one aspect, a system for corneal condition diagnosis and anterior segment conditions includes a memory that stores instructions, and a processor that executes the instructions to perform operations. The operations may include inputting input data including an image or map into an AI model, processing the input data, and generating a set of scores and outputting a prediction. The AI model may comprise a plurality of convolutional layers, a fully connected layer, and an output layer. The image or map may be representative of a cornea or anterior segment of an eye. Processing the input data may include processing the data through the plurality of convolutional layers, the fully connected layer, and the output layer. Each score of the set of scores may be generated by a corresponding node in the output layer. The output prediction may be related to the cornea or anterior segment of the eye represented by the input data processed through the plurality of convolutional layers, fully connected layer, and output layer of the AI model. The prediction may be determined by at least one score of the set of scores.

In one example, the input data comprises input data comprises at least one of an OCT B-scan of the cornea or anterior segment of the eye, a color image of the cornea or anterior segment of the eye, a thickness map corresponding to one or more corneal layers of the eye, a bullseye map corresponding to one or more corneal layers of the eye, a heat map corresponding to one or more corneal layers of the eye, a map of the cornea representing contours or curvature of the cornea or one or more of its layers, or a map representing relative contour, curvature or elevation of the cornea or one or more of its layers relative to each other or relative to a defined sphere, surface, or curve.

In a further example, the set of scores comprises a set of condition scores, wherein each condition score specific to a particular cornea or anterior segment condition or disease. The condition scores may correspond to a calculated likelihood that the cornea or anterior segment of the eye represented by the input data has the particular cornea or anterior segment condition or disease to which the condition score is specific. In a further example, the particular cornea or anterior segment conditions or diseases to which the condition scores are specific comprise corneal ectasia, corneal graft rejection episode and failure, dry eye syndrome (DES), Fuchs' dystrophy, corneal limbal stem cell deficiency, cataract, glaucoma, or combinations thereof. In any of the above or another example, the set of scores includes a score that at least one of: corresponds to a likelihood of a severity of the particular corneal or anterior segment condition or disease to which one of the condition scores is specific; corresponds to a severity score of the particular corneal or anterior segment condition or disease to which one of the condition scores is specific; corresponds to a likelihood that the cornea or anterior segment of the eye represented in the input data will develop the particular corneal or anterior segment condition or disease to which one of the condition scores is specific; corresponds to the likelihood that the cornea or anterior segment of the eye represented in the input data will respond favorably or unfavorably to treatment for the particular corneal or anterior segment condition or disease to which one of the condition scores is specific; or assists or guides a physician decision to utilize a specific treatment technique for the particular corneal or anterior segment condition or disease to which one of the condition scores is specific. In one example, the prediction comprises a diagnosis of more than one cornea or anterior segment condition or disease with respect to the cornea or anterior segment of the eye represented by the input data when the condition scores for multiple cornea or anterior segment conditions or diseases are above thresholds corresponding to those conditions or diseases.

In any of the above or another example, the operations further comprise processing input data comprising multiple B-scan images of the cornea or anterior segment of the eye, and generating a set of condition scores for each B-scan. Each set of condition scores may include a condition score corresponding to a particular cornea or anterior segment condition or disease. The prediction may include a mean of the condition scores corresponding to the particular cornea or anterior segment condition disease from each set of condition scores. In a further example, multiple B-scan images may be taken along multiple cuts of the cornea or anterior segment of the eye.

In any of the above or another example, the set of scores comprises a set of severity scores specific to a particular cornea or anterior segment condition or disease, wherein each severity score is specific to a severity level for the particular cornea or anterior segment condition or disease to which the set of severity scores is specific. In this or another example, the set of scores comprises a severity score specific to a particular cornea or anterior segment condition or disease, and wherein the prediction comprises the severity score. In any of the above or another example, the set of scores is specific to a particular cornea or anterior segment condition or disease and comprises a set of risk scores, each risk score specific to a risk level with respect to progression of the particular cornea or anterior segment condition or disease to which the set of scores is specific, and the prediction comprises a discrete value or category corresponding to at least one of the risk levels. In any of the above or another example, the set of scores is specific to a particular cornea or anterior segment condition or disease and comprises a set of action scores, each action score specific to a particular action with respect to the particular cornea or anterior segment condition or disease to which the set of scores is specific, and the prediction comprises a discrete value or category corresponding to at least one of the actions. In any of the above or another example, the set of scores is specific to a particular cornea or anterior segment condition or disease and comprises a set of treatment scores, each treatment score specific to a particular treatment with respect to the particular cornea or anterior segment condition or disease to which the set of scores is specific, and the prediction comprises a discrete value or category corresponding to at least one of the treatments.

In any of the above or another example, the operations further include training the AI model with B-scan images without averaging or registration to increase robustness to noise. In any of the above or another example, the input data includes an OCT B-scan image, and the operations further comprise preprocessing the OCT B-scan images to remove artifacts. In any of the above or another example, the input data comprises a series of B-scan In any of the above or another example, the system further comprises an analysis subsystem to generate a health report comprising a prediction with respect to cornea or anterior segment condition or disease and one or more of a severity of the prediction corneal or anterior segment condition or disease; a severity score of the predicted corneal or anterior segment condition or disease to which one of the condition scores is specific; a likelihood that the cornea or anterior segment of the eye represented in the input data will develop the predicted corneal or anterior segment condition or disease; or a likelihood that the cornea or anterior segment of the eye represented in the input data will respond favorably or unfavorably to treatment for the predicted corneal or anterior segment condition or disease.

In any of the above or another example, the system further includes a preprocessing subsystem comprising a map generator, and wherein the operations further comprise generating the input data, and wherein generating the input data comprises generating a thickness map, heat map, or bullseye map of one or more layers of the cornea from an OCT B-scan or color image. In a further example, the operations further comprise inputting the OCT B-scan or color image into another AI model to automatically segment the one or more layers before generating the thickness map, thickness map, or bullseye map from the segmented OCT B-scan or color image.

In any of the above or another example, the operations further include generating a health report using the set of scores from a current processing of input data and a previous processing of input data. The current and previous processed input data may correspond to the same cornea or anterior segment of the same eye.

In any of the above of another example, the system includes an ensemble of submodels. The ensemble of submodels may be trained for obtaining a same predictive category or class. The operations may include processing the input data through each of the ensemble of submodels, and wherein the prediction comprises a combined output of the ensemble of submodels.

In any of the above or another example, the AI model includes an augmented model. The output layer of the augmented model may output a set of scores corresponding to augmented categories. Each augmented category may correspond to a disease or condition of the cornea or anterior segment of eye and at least one ancillary aspect related to the disease or condition. In one embodiment, the ancillary aspect related to the disease or condition comprises severity, risk, action, treatment, progression, or combination thereof.

In any one of the above or another example, the input data comprises first input data representative of a cornea or anterior segment of a right eye of an individual and second input data representative of a cornea or anterior segment of a left eye of the individual. The prediction as to one of the left or right corneal or anterior segments may be based on the set of scores generated from both the first and second input data.

In any of the above or another example, the input data includes a temporal sequence of B-scan images. In any of the above or another example, the input data further includes patient data comprising medical or demographics data.

In any of the above or another example, the operations further include identifying a region in the input data having the highest correlation to a prediction accuracy. In one further example, identifying regions of the input data having the highest correlation to prediction accuracy includes processing the input data with different regions of the data occluded from the processing and deeming regions corresponding to the largest drops in prediction accuracy compared to the input data without occlusion as the regions having the highest correlation to prediction accuracy. In a further example, the operations may further include introducing spatial weighting into the AI model to increase importance of a region to a specific prediction. The region in which the importance is increased is a region identified to have high correlation to the prediction accuracy for the specific prediction.

In another aspect, a method of generating a diagnosis with respect to a disease or condition of a cornea or an anterior segment of an eye includes inputting input data comprising an image or map into an AI model, processing the input data, and generating a set of scores and outputting a prediction. The AI model may comprise a plurality of convolutional layers, a fully connected layer, and an output layer. The image or map may be representative of a cornea or anterior segment of an eye. Processing the input data may include processing the data through the plurality of convolutional layers, the fully connected layer, and the output layer. Each score of the set of scores may be generated by a corresponding node in the output layer. The output prediction may be related to the cornea or anterior segment of the eye represented by the input data processed through the plurality of convolutional layers, fully connected layer, and output layer of the AI model. The prediction may be determined by at least one score of the set of scores.

In yet another aspect, a non-transitory computer-readable device comprising instructions, which when loaded and executed by a processor, may cause the processor to perform operations including inputting input data comprising an image or map into an AI model, processing the input data, and generating a set of scores and outputting a prediction. The AI model may comprise a plurality of convolutional layers, a fully connected layer, and an output layer. The image or map may be representative of a cornea or anterior segment of an eye. Processing the input data may include processing the data through the plurality of convolutional layers, the fully connected layer, and the output layer. Each score of the set of scores may be generated by a corresponding node in the output layer. The output prediction may be related to the cornea or anterior segment of the eye represented by the input data processed through the plurality of convolutional layers, fully connected layer, and output layer of the AI model. The prediction may be determined by at least one score of the set of scores.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the described embodiments are set forth with particularity in the appended claims. The described embodiments, however, both as to organization and manner of operation, may be best understood by reference to the following description, taken in conjunction with the accompanying drawings in which:

FIGS. 2A-2C are examples of input data wherein FIG. 2A is an OCT B-scan, FIG. 2B is a thickness map showing total cornea thickness, and FIG. 2C is a bullseye map showing total cornea thickness according to various embodiments;

FIGS. 3A & 3B illustrate a preprocessing operation of an input image wherein image artifacts shown in the image of FIG. 3A are removed as shown in the image of FIG. 3B according to various embodiments described herein;

FIG. 19A is a schematic diagram of an embodiment of the system including an augmented category AI model according to various embodiments;

FIG. 19B is table representing augmented categories for an augmented category AI model described with respect to FIGS. 19A & 19C according to various embodiments;

FIG. 19C is a schematic diagram of an embodiment of the system including an augmented category AI model described with respect to FIG. 19A according to various embodiments;

DESCRIPTION

Artificial Intelligence (AI) entails the development of computer systems capable of performing tasks that requires human intelligence, such as visual perception, speech recognition, and decision-making. These tasks need cognitive functions associated with human minds, namely learning and problem solving.

Machine learning is a subset of AI. Machine learning may be implemented utilizing Deep Learning (DL). DL is a machine learning method that employs mathematical models called neural networks. Neural networks may include large number of layers that attempt to mimic the human brain. In operation, DL attempts to extract complex hierarchal features and patterns present in large datasets. These features may then be merged together using neural networks to represent the model of the data.

Described herein are AI-based systems and methods for corneal diagnosis, such as assisting in the diagnosis or treatment of corneal disease or conditions. The AI-based systems and methods utilize machine learning. For example, systems and methods may utilize AI models in machine learning to automate diagnosis, for example utilizing deep learning models. The systems and methods described herein may be implemented as standalone or integrated applications for processing images or maps such as Optical Coherence Tomography (OCT) images or B-scans, thickness maps, bullseye maps, curvature maps, topography maps, tomography maps, or elevation maps of the human cornea and/or the anterior segment of the eye using Artificial Intelligence models associated with image data. One method includes obtaining a model that takes single B-scan of a human cornea as input and outputs the diagnosis of this cornea or anterior segment. The diagnosis includes the prediction of the disease or condition, the prediction of the severity level and the detection of the important features in the input B-scan. Another method includes obtaining a model that takes thickness map, heat map, or bullseye map of specific layer of a human cornea and outputs the diagnosis of this cornea. The diagnosis includes the prediction of the disease or condition, the prediction of the severity level and the detection of the important regions in the input thickness map. A third method includes obtaining a model that takes a B-scan of a human cornea and outputs the segmentation of layer boundaries of the cornea in this B-scan. The outputs for a whole scan can then be used to obtain the thickness maps from which heat maps, bullseye maps, or structure maps may be generated.

Figure 1A:
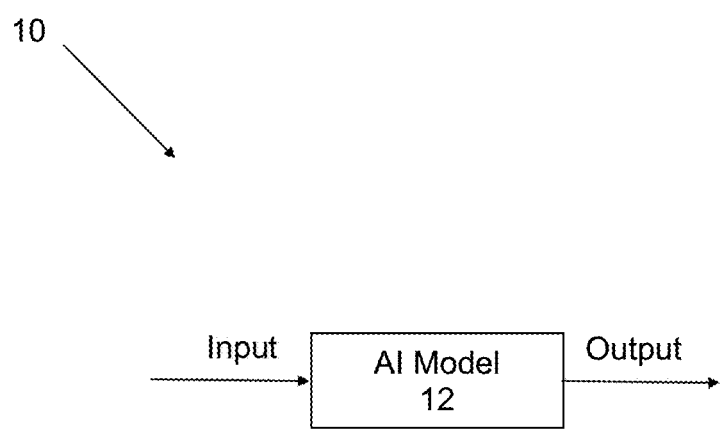
FIG. 1A is a schematic diagram of an embodiment of the system comprising an AI model configured to perform a prediction operation according to various embodiments.

FIG. 1A schematically illustrates an embodiment of the system 10 configured to perform a prediction operation according to various embodiments.

Broadly, the system 10 receives data input which is processed through an AI models 12 to generate an output prediction. In operation, the system 10 may execute the prediction operation to diagnose the presence of a certain pathology or its absence in the human cornea or anterior segment of the eye. The data input may include various data such as color and/or high resolution images of the cornea or anterior segment. Data inputs may also include data inputs used for training, testing, and/or tuning the AI model 12 for generating predictions or other system outputs.

In some embodiments, the system 10 is configured to predict one or more diseases or conditions, if any, in the human cornea and/or predict the severity of disease or condition using an input image. Other or additional inputs may also be used. For example, input data may include patient data such as demographic data or medical data, e.g., data relating to a condition of a patient's other cornea or prior condition of state of the imaged cornea. Herein, the terms condition and disease, with respect to the cornea or anterior segment, may be used interchangeably.

Figure 1B:
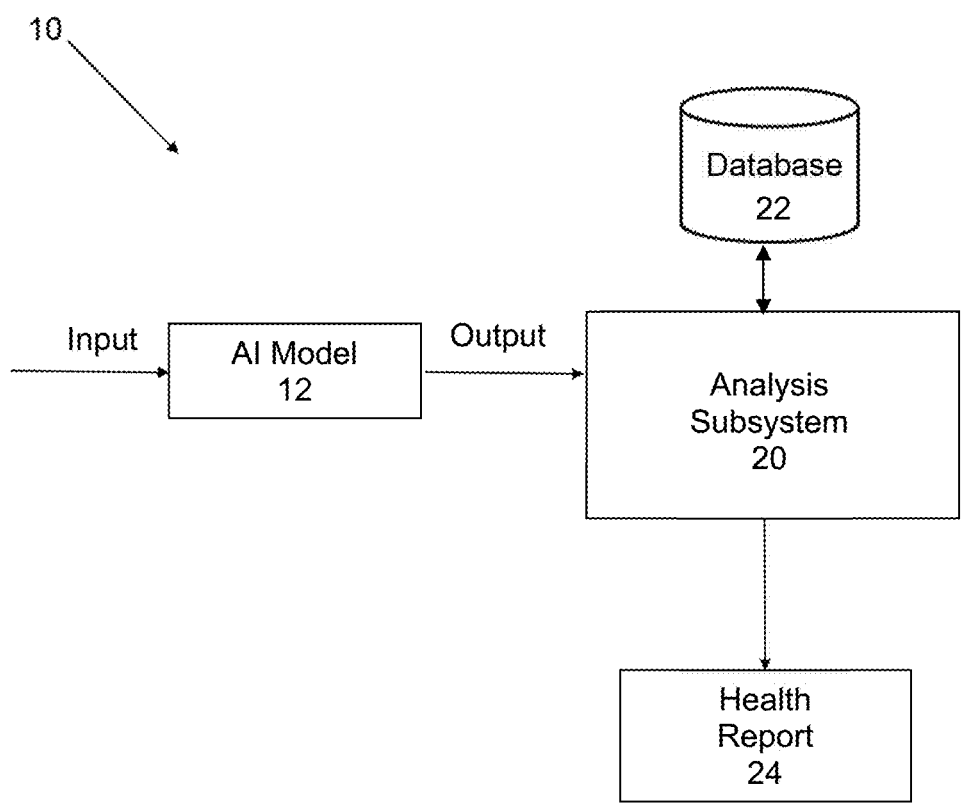
FIG. 1B is a schematic diagram of an embodiment of the system including an AI model configured to perform a prediction operation and including an analysis subsystem according to various embodiments.

FIG. 1B schematically illustrates an embodiment of the system 10 of the system 10 configured to perform a prediction operation. The system 10 is similar to the system 10 described with respect to FIG. 1A and further includes an analysis subsystem 20. The analysis subsystem 20 is configured to receive the AI model 12 output. The analysis subsystem 20 may store the output in a system database 22. The analysis subsystem 20 may also generate a cornea or anterior segment health report including the output. For example, the health report may include a predicted diagnosis. In some embodiments, the health report 24 may include the current output and a history of old outputs for the cornea or each cornea of a patient. In some embodiments, history such as old outputs may be stored in the database 22 for access by the analysis subsystem 20 for analysis and/or inclusion in health reports 24. The analysis subsystem may be connected to the AI model 12, which may include multiple networks or models, to generate a report. Thus the outputs of various networks or modules of the AI model 12 may be analyzed by the analysis subsystem 20. The networks or models of the AI model 12 may be referred to herein interchangeably, but are generally referred to as submodels for brevity. Submodels may also include multiple submodels. Submodels may be integrated, e.g., may include combined or shared model layers or may feed or be fed by other submodel output scores or predictions. Integrated models may be referred to herein as combined, joint, or combination models or networks, for example. In some embodiments, the AI model integrates out of system AI networks or models, and/or databases, which may include system databases 22, third party databases, or combinations thereof.

Figure 2A:
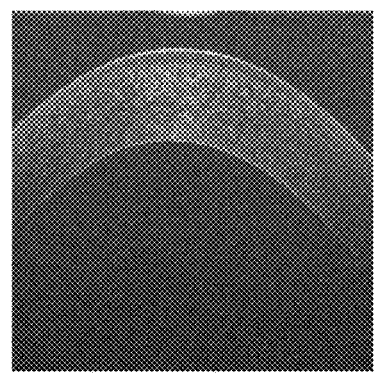
Figure 2B:
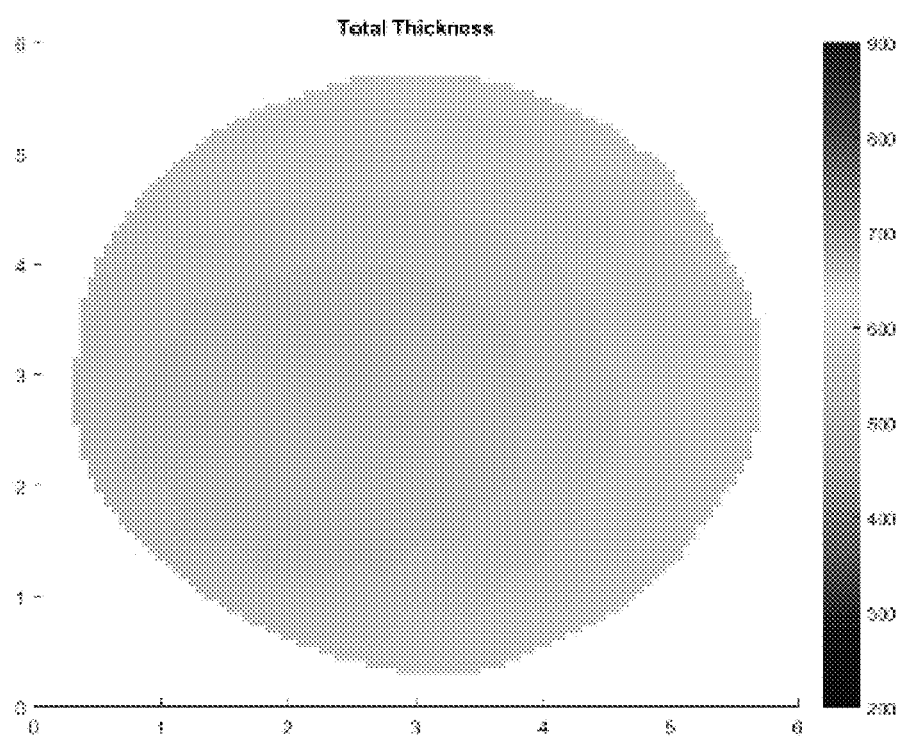

As introduced above, the input data may include images or maps. In various embodiments, and with further reference to FIGS. 2A-2C, the system 10 may employ AI techniques in Optical Coherence Tomography (OCT). The techniques may be further extended to corneal microlayer tomography, which may be performed utilizing OCT images and processing of OCT images. For example, the AI model 12, or one or more submodels thereof, may take an input such as one or more OCT B-scans (FIG. 2A), thickness maps (FIG. 2B), bullseye maps (FIG. 2C), heat maps, color coded maps, and/or color images of the cornea and anterior segment and then output a prediction. Input data may also include maps such as curvature maps, topography maps, or tomography maps, or elevation maps. For example, input data may include a map of the cornea representing contours or curvature of the cornea or one or more of its layers. In a further example, the input data includes a map representing relative contour, curvature or elevation of the cornea or one or more of its layers relative to each other or relative to a defined sphere, surface, or curve. These maps may be produced by application of mapping techniques to images such as OCT images or other high-definition images. Some maps may be produced devices such as corneal Placido disc topographers or Pentacam® rotating Scheimpflug cameras.

In various embodiments, B-scans may be obtained using an OCT imaging system comprising an OCT imaging machine for producing high-definition images. One example, OCT imaging machine is an OCT Bioptigen Envisu™ R-Class machines marketed by Leica Microsystems, Wetzlar, Germany. A B-scan is cross-sectional image captured by an OCT machine that represent one cut (for example, horizontal or diagonal) in eye. The cut may be horizontal or diagonal for example. In various embodiments, the image could include the cornea, anterior segment or other structures of the eye. As introduced above, a B-scan is a cross-sectional OCT image for a specific cut in the cornea and anterior segment and may be assembled from sequential A-scans (axial scans) along the cut. The input image data may also include OCT images assembled by projecting a sequence of A-scans obtained using an OCT machine. In a further embodiment, input data may include an image data comprising a projection of a series of B-scans into one image, e.g., a three dimensional image of the cornea or one or more layers thereof. A volume OCT scan is a complete series of B-scans that span the entire cornea or anterior segment of the patient. It can be raster or radial scans for example. A thickness map may be generated from B-scans, such as a volume OCT scan. In one example, a thickness map may be generated by a subsystem or the system 10 or by a separate system that takes as input a volume OCT scan. A thickness map may include a map of total corneal thickness. The layer boundaries in the thickness map may be segmented the layer boundaries in the B-scans and convert them to heat maps that represent the thickness for individual corneal layers or combinations thereof. In still further embodiments, input data includes input image data comprising a B-scan of individual or combinations of individual corneal layers, e.g., a segmented B-scan or B-scan of one or more isolated layers of a B-scan.

A map or data map may include a map of an anterior segment, cornea, or one or more layers thereof. The map may include thickness data or data derived therefrom. For example, a data map may include thickness data representative of one or more layers of the cornea. A data map also include thickness ratios or comparisons with respect to one or more regions of one or more layers of the cornea, to normal data, to other data from another part of the cornea or later of the cornea, or indices, for example. Such maps may be referred to as thickness maps.

A thickness map is a generated image or data description showing the thickness at different points of a layer of the cornea or may include a 3D map or data description representing many layers of the cornea. For example, a thickness map may include thickness data with respect to all corneal layers, a single layer, or a combination of layers. In various embodiments, a thickness map depicts thickness data as raw calculated thickness. In some embodiments, a thickness map depicts thickness data using ratios or deviations from normal data or a minimum, mean, max, or median thickness of the cornea or a layer or region thereof. Thickness maps may depict thickness data using color, e.g., in a heat map, with numbers, or other manner of presenting the data. In one embodiment, a thickness map comprises a three dimensional image or numerical data representation of one or more layers of the cornea depicting the thickness data. In one embodiment, a thickness map includes a graph depicting thickness data along one or more layers of the cornea. Further to the above, a thickness map may include data representative of topography or contour, shape, relative thickness, or patterns thereof, which may include comparisons among or between layers, for example. In one example, the system 10 includes diagnosis for keratoconus. The system 10 may be trained and/or configured to receive data inputs for predictions comprising thickness maps indicating contours or contours compared to normative data. In another example, the system 10 is configured for diagnosis of graft rejection and the system 10 may be trained and/or configured to receive data inputs for predictions comprising thickness maps showing thickness data such as comparisons of thickness data or one or more layers to normative data and further comparisons of thickness of endothelial/Descemet's layer relative to other layers and/or to expected thickness relative to other layers based on normative data.

Bullseye maps are generally a vector of numbers summarizing a thickness map for the cornea or one or more corneal layers. A bullseye map may be generated to abstract thickness maps locally by representing each specific region by its mean, maximum, median, ratio, index value, for example. These regions are usually formed by dividing thickness maps into sectors or sector-segments. In various embodiments, the numbers may represent a calculated, ratio, or deviation therefrom, mean, min, max, median, ratio between thickness in a region and another, or a ratio between thickness in a region and normal data of several divisions of the thickness map. In some examples, the system 10 may be configured bullseye map inputs incorporating mean, mode, range, standard deviation, variance, or index calculation for all layers, a single layer, or combinations of layers or regions of the cornea.

Thickness maps and/or bullseye maps may be generated by processing B-scans, e.g., using software to interpolate thicknesses from a series of B-scans. In some embodiments, as described in more detail below, the system 10 may be configured to generate thickness maps, bullseye maps or both for input into the AI model 12. It will be appreciated that the system 10 may be configured to utilize many forms of input data. Such data may include images or data representations of or data derived from the images.

Maps may also include elevation, curvature, topographical or contour data maps, and which may be referred to generally as structure maps and which may include maps of the cornea representing contours or curvature of the cornea or one or more of its layers. Such maps may also represent relative contour, curvature or elevation of the cornea or one or more of its layers relative to each other or relative to a defined sphere, surface, or curve. Devices that may produce these maps include corneal Placido disc topographers or Pentacam® rotating Scheimpflug cameras.

Figure 1C:
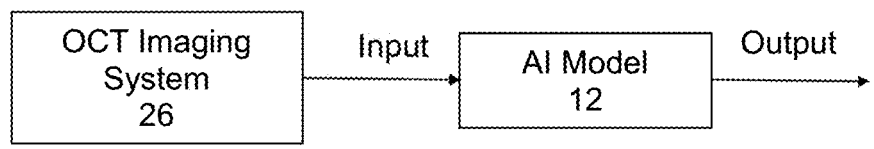
FIG. 1C is a schematic diagram of an embodiment of the system including an OCT imaging system and an AI model configured to perform a prediction operation according to various embodiments.
Figure 1D:
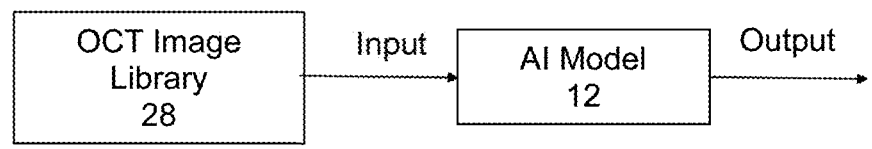
FIG. 1D is a schematic diagram of an embodiment of the system including an OCT image library and AI model configured to perform a prediction operation according to various embodiments.

With further reference to FIGS. 1C & 1D, in some embodiments, the system 10 includes or is in communication with an OCT imaging system 26 configured to obtain OCT images of a cornea or anterior segment (FIG. 1C) and/or an OCT image library 28 comprising OCT images of a cornea or anterior segment (FIG. 1D). OCT images, such as B-scans or color images, may be provided for input into the AI model 12 from the OCT imaging system 26 and/or OCT image library 28.

Figure 1E:
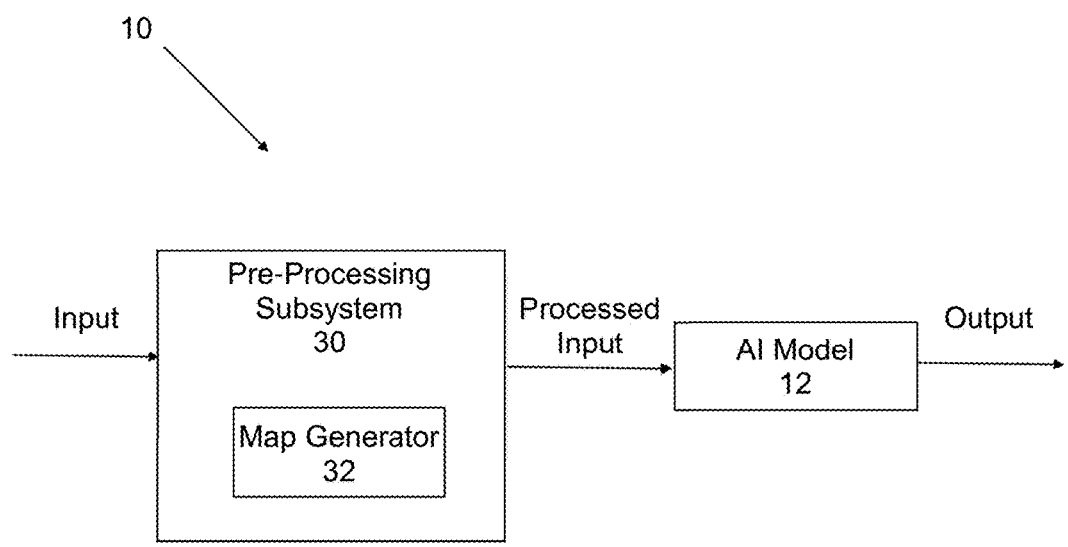
FIG. 1E is a schematic diagram of an embodiment of the system including a preprocessing subsystem and an AI model configured to perform a prediction operation according to various embodiments.

As introduced above, the input data may include images or maps, such as thickness maps, heat maps, bullseye maps, or structural maps. Such maps may be provided to the system 10 or may be generated by the system 10. For example, as schematically illustrated in the embodiment shown in FIG. 1E, the system 10 may include a preprocessing subsystem 30 configured to preprocess data for input into the AI model 12. The preprocessing subsystem 30 may include a map generator 32. The preprocessing subsystem 30 or map generator 32 may comprise a processor and memory that stores computer readable instructions, such as firmware/software, executable by the processor to generate thickness maps, heat maps, bullseye maps, or structural maps for input into the AI model 12. As described in more detail below, a preprocessing subsystem 30 may include another AI model. In various embodiments, generation of bullseye maps, heat maps, and/or thickness maps, which may include color coded maps, or combinations thereof, of one or more corneal layers, may be performed by computer readable instructions executed by the processor according to the systems and methods disclosed in U.S. patent application Ser. No. 15/868,856, titled "Method and System for Three-Dimensional Thickness Mapping of Corneal Micro-Layers and Corneal Diagnosis," filed Jan. 11, 2018, the contents of which are hereby incorporated herein by reference. In one embodiment, the OCT imaging system 26 (see, e.g., FIG. 1C) may include a map generator 32. The OCT imaging system 26 or map generator 32 may comprise a processor and memory storing computer readable instructions executable by the processor to generate thickness maps, heat maps, bullseye maps, or structural maps from OCT images that may be input for processing through the AI model 12. In one embodiment, the system 10 may be configured to receive and/or request generation of maps. For example, the system 10 may communicate with a map generation API to receive and/or request generation of maps with respect to OCT images.

Figure 1F:
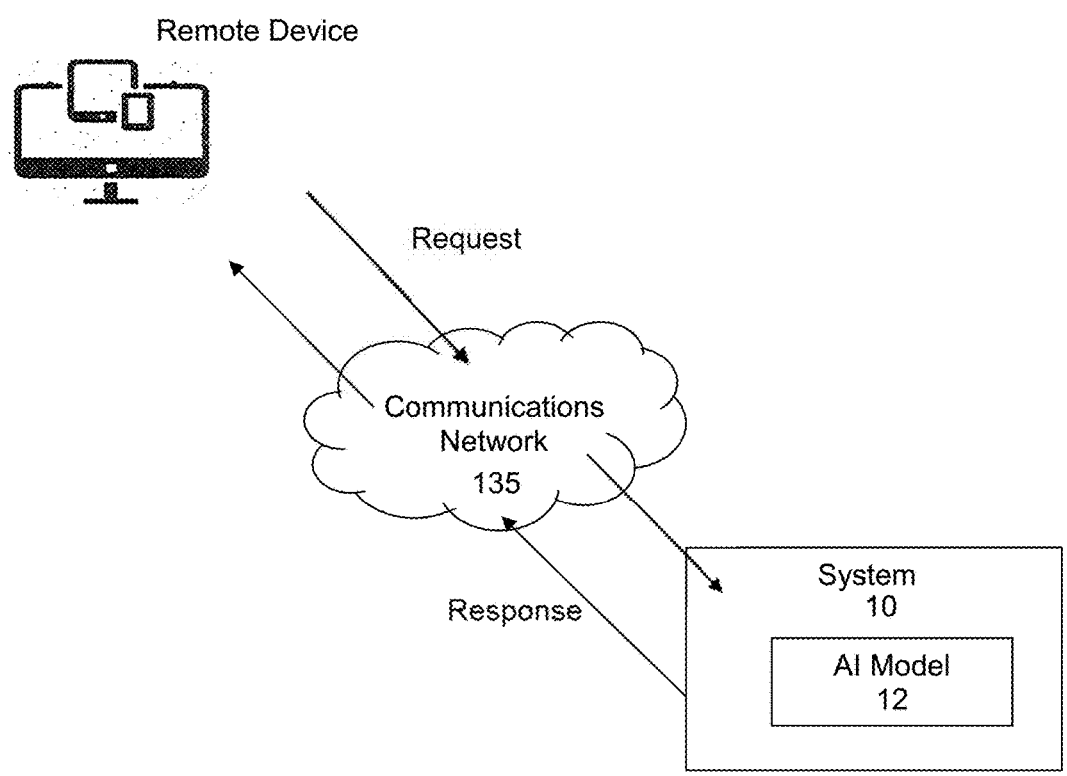
FIG. 1F is a is a schematic diagram of an embodiment of the system including a remotely accessible AI model configured to receive requests for cornea or anterior segment predictions and generate such predictions according to various embodiments.

FIG. 1F schematically illustrates a further embodiment of the system 10 wherein the AI model 12 or one or more submodels thereof is remotely accessible. For example, the AI model 12 may be configured to receive requests for cornea diagnosis from remote device 40. The remote device 40 may include, for instance, a computer on which an image capturing system, such as an OCT imaging system 26, is implemented configured to submit a requests to the system 10 over an electronic communication network 135 by providing input image as part of making an Application Programming Interface (API) call to the system 10. Upon receiving the request, the system 10 may input the input data and generate the cornea or anterior segment data analysis and transmit it back to the remote device 40. In various embodiments, the remote device 40 may provide OCT images such as one or more B-scans for input into the AI model 12. In some instances, the remote device 40 may provide thickness maps, heat maps, bullseye maps, or structural maps or may request that a set of B-scans be used to generate such maps. For example, the system 10 may include or be in communication with a map generator, such as the map generator 32 of the preprocessing subsystem 30 described above with respect to FIG. 1E or map generator API. In one embodiment, the system 10 comprises one or more electronic communication devices configured to communicate the AI model 12, such as one or more submodels thereof, implemented on one or more remote computers. The system 10 may access the AI model 12 by making an API call over a network. The call may include a request for a prediction using the AI model 12 based on one or more input data. In one example, the request identifies or includes input data for input into the AI model 12. The input data may be processed through the AI model 12 and the output may be transmitted back to the system 10 in response to API call.

It will be appreciated that the various embodiments of the system 10 described above and elsewhere herein, including those described with respect to the drawings, may include any combination of the various features highlighted herein. For example, one embodiment of the system 10 may include one, more, or all of an OCT imaging system 26, OCT image library 28, preprocessing subsystem 30, map generator 32, analysis subsystem 20, and/or output database 22 described with respect to FIGS. 1B-1E. In one further embodiment, the system 10 described with respect to FIG. 1F further includes an analysis subsystem 20 configured to generate a health report 24 and provide the health report 24 to a system user. The system 10 may further include a database 22 (see FIG. 1B) for storing the output from the AI model 12 and/or storing historical outputs for use in generating the health report. In one example, the user may provide or identify historical outputs in the request or in a separate submittal.

Figure 1G:
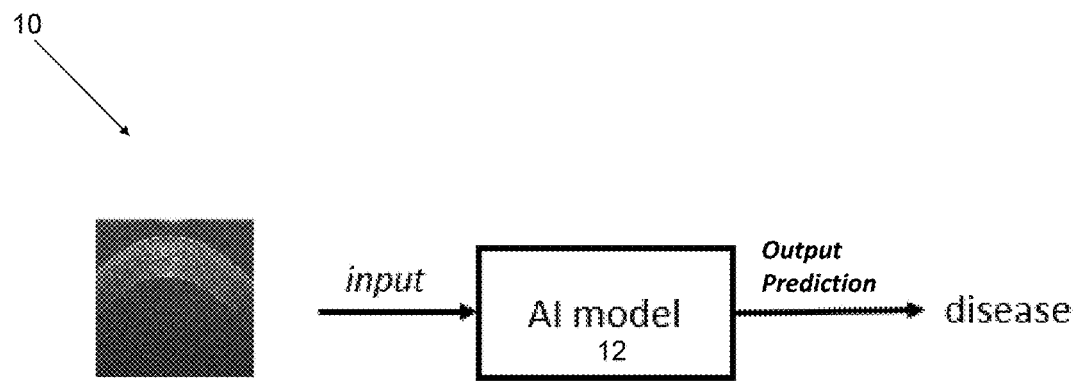
FIG. 1G is a schematic diagram of an embodiment of the system including an AI model trained for predicting the presence of one or more corneal or anterior segment diseases or condition using images as input according to various embodiments.
Figure 1H:
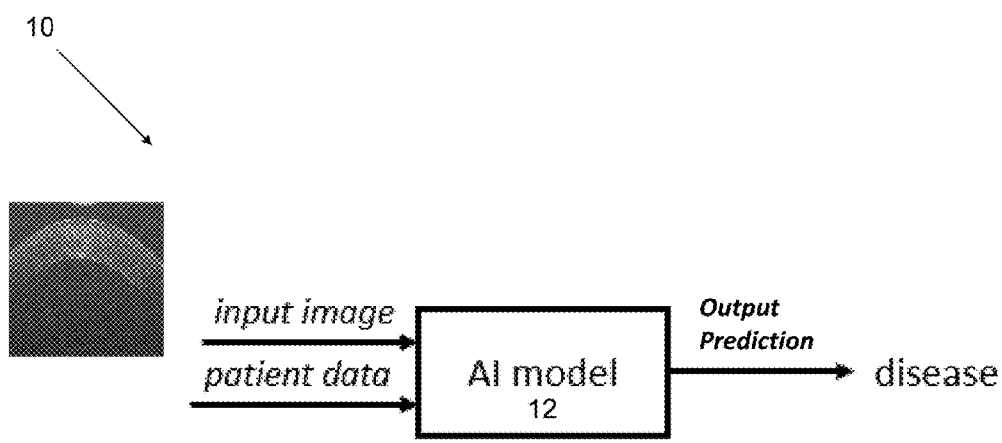
FIG. 1H is a schematic diagram of an embodiment of the system including an AI model trained for predicting the presence of one or more corneal or anterior segment diseases or condition using images and patient data as inputs according to various embodiments.
Figure 1I:
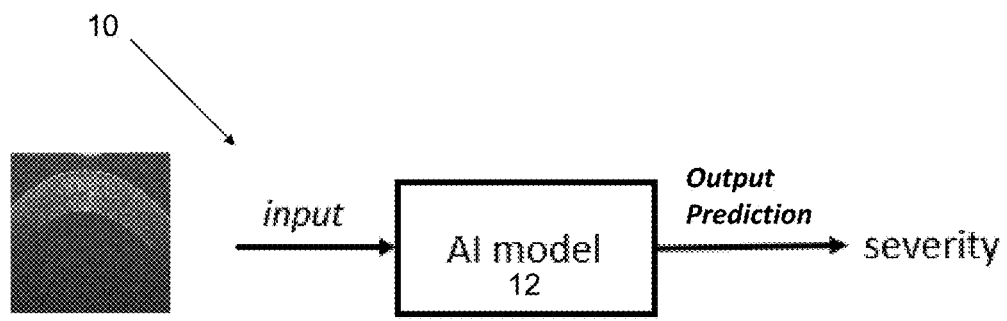
FIG. 1I is a schematic diagram of an embodiment of the system including an AI model trained for predicting the severity of one or more corneal or anterior segment diseases or condition using images as input according to various embodiments.
Figure 1J:
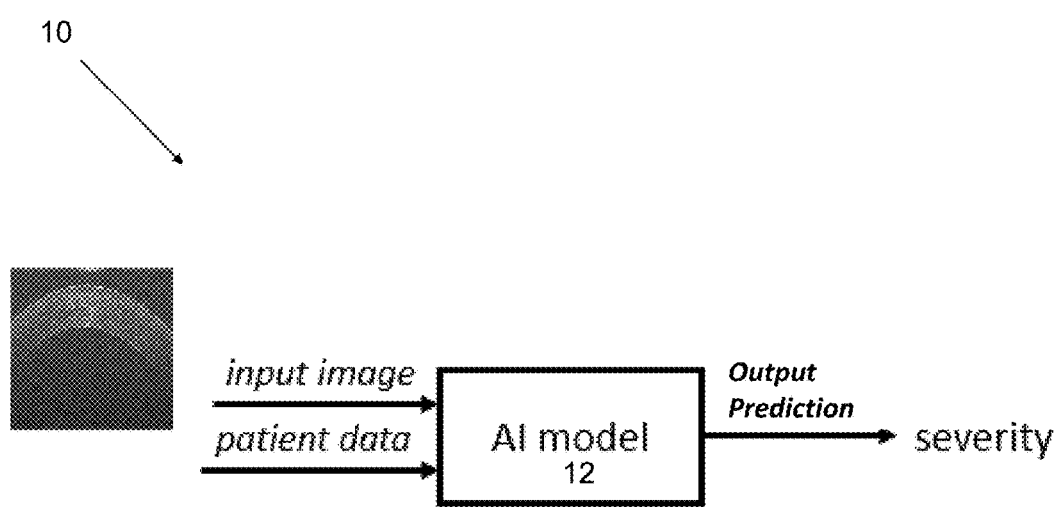
FIG. 1J is a schematic diagram of an embodiment of the system including an AI model trained for predicting the severity of one or more corneal or anterior segment diseases or condition using images and patient data as inputs according to various embodiments.

FIGS. 1G-1J schematically illustrate embodiments of the system 10 for generating a prediction. In the illustrated operations, the system 10 is provided input data related to a cornea or anterior segment and the data is processed through an AI model 12 to generate a prediction of a corneal or anterior segment condition or disease (FIGS. 1G-1H) or severity of a disease of condition (FIGS. 1I-1J).

As introduced above, the form of the input data may comprise one or more images, such as medical images. Maps may also be used instead or in addition to images in some embodiments. Input data may include, for example, one or more of OCT corneal microlayer tomography B-scans (CML-T), thickness maps, heat maps, bullseye maps, or structural maps of the cornea and/or one or more of its layers. Thickness maps and bullseye maps may be maps generated from evaluation or analysis of high-definition images of the cornea.

With respect to FIGS. 1G-1J, each embodiment comprises an AI model 12 trained to process input data comprising an OCT B-scan and, optionally, other patient data to product the prediction. The input image may be of a patient's cornea or anterior segment of the eye. In particular, the system 10 shown in FIG. 1G includes an AI model 12 trained for predicting the presence of one or more corneal or anterior segment diseases or condition using input data comprising a B-scan input image. The system 10 shown in FIG. 1H includes an AI model 12 for predicting the presence of one or more corneal diseases or conditions using input data comprising an OCT B-scan and patient data. In particular, the system 10 shown in FIG. 1I includes an AI model 12 trained for predicting severity of one or more corneal or anterior segment diseases or condition using input data comprising a B-scan input image. The system 10 shown in FIG. 1J includes an AI model 12 for predicting severity of one or more corneal diseases or conditions using input data comprising a B-scan and patient data. In some of the above or other embodiments, the input data may include other or additional input data as described herein. While the input data shown in the embodiments illustrated in FIGS. 1G-1J comprise OCT B-scans; in some implementations, instead of or in addition to one or more OCT B-scans, the input data includes one or more thickness maps, heat maps, bullseye maps, structural maps, color images, and/or other high-definition medical images.

The number of image data the system 10 may input to generate a prediction may depends on the implementation of the one or more AI models 12 of the system 10. For example, in some embodiments, the input image data includes a single image that captures a current state of a patient's cornea or anterior segment. In one such embodiment, the system 10 includes an AI model 12 comprising a feedforward neural network model that has been trained on labeled training data to process the input image and/or the other patient data to generate a model output.

As introduced above, FIGS. 1H & 1J illustrate embodiments of the AI model 12 configured generating predictions based on input data comprising one or more input images and other patient data. In various embodiments, the other patient data may include, for example, medical data, demographical data, or both. Medical data may include, for example, corneal curvature, central corneal thickness, eye pressures, visual fields, or visual acuity, among others. Demographical data may include, for example, age, gender, ethnicity, past medical history, family history, or occupation, among others.

With continued reference to FIGS. 1A-2C, and as applicable to the other embodiments described herein, in some embodiments, input image data includes multiple images that capture a current state of a patient's cornea or anterior segment. For example, the input image data may include multiple B-scan images taken along a same cut or multiple cuts of the cornea or anterior segment. In this or another example, the input image data may include a sequence of images as a temporal sequence. In any of the above or another example, the input data may include multiple B-scan images comprising one or more images of the patient's left and right corneas or anterior segment. In one embodiment, the AI model 12 may predict a diagnosis likelihood that is generated based on input data related to the condition of the other eye of the patient. Such data may include indication of the presence of a condition of the other eye, location, severity, characteristics, maps, or images of the other eye. In one example, images of the other eye may be utilized by the AI model 12 for comparison or feature correlations. Some conditions or diseases may be more likely bilateral but usually asymmetrical, e.g., keratoconus and Fuchs dystrophy. Presence of the disease in one eye makes the other more likely to have the same condition but with different severity or sometimes in a sub clinical form. Thus, the presence of the disease in one eye may be incorporated as a weight that can be multiplied by the probability of the diagnosis in the other eye. Weight may be determined by incidence data or by a subsystem comprising an AI model that determines the bilaterally probability from existing training data. In some instances, patient data such as demographics may similarly be incorporated. In some embodiments, recurrent neural networks or Bayesian networks may be used to model such data.

In some embodiments wherein the input data includes multiple images, the system 10 may include a feedforward AI model 12 that has been trained on labeled training data to process all the input images to generate a model output.

In various embodiments, the AI model 12 takes as input images of both eyes, which may include B-scans, thickness maps, heat maps, bullseye maps, or structural maps, for example. The output probabilities of each data input may be used to weight or modify the output probabilities of one or more of the other probabilities. As described above and elsewhere herein the AI model 12 may include multiple submodels. The submodels may be integrated into one or more submodels. In some embodiments, multiple submodels may be combined by feed forward of input, scores, or predictions into subsequent submodels. In one embodiment, multiple submodels may be combined by integration of various layers, blocks of layers, or combinations of layers or blocks. Inputs may include multiple image types or data forms, which may include patient data such as demographics data. Multiple inputs may be input at various stages of the AI model 12. For example, additional data inputs may be input as weights within fully connected layers or applied as multipliers of scores of one or more submodels. In one example, the AI model takes as input images of both eyes, e.g., one or more B-scans of each eye and/or one or more heat maps of one or both eyes. The AI model may predict disease in one eye which may increase the probability of disease in the other eye. In one example, the probability that the patient has a disease or condition may include multiplying the probability of the disease in each eye.

In one embodiment, the accuracy of the system 10 may be improved utilizing multiple B-scans of the same eye. For example, the system 10, or an analysis subsystem thereof, may calculate a probability of a diagnosis for each single B-scan and then calculate a mean of the probabilities from the total B-scans of the same eye. The averaging may be taken from independent predictions generated for each scan.

In any of the above or a further embodiment, input data may include one or more maps, e.g., thickness maps, heat maps, bullseye maps, or structural maps, as introduced above. Such maps may be provided in addition to one or more images and/or patient data. In one example, the maps may be of one or more cornea layers or total cornea. Graft rejection of the cornea, for example, may be marked by general global thickening of the cornea and more substantial thickening of the endothelial layer/Descemet's membrane relative to the rest of the cornea. Thus, input data may include total cornea thickness maps and/or thickness maps of each layer. Keratoconus is another example where a specific pattern of thickening of the epithelium at the area where the stroma and Bowman's layers may be thinned. These patterns of relative thickening and thinning are difficult to represent with an index but may be detected by the AI model 12 that looks at the thickness data of all the layers at the same time and detects such patterns.

In yet other embodiments, the image data includes a temporal sequence of images taken at different time that capture how the cornea state has evolved. Such image data may be used with respect to AI models 12 trained to predict effective treatment, effectiveness of current or future treatments, recovery time, disease of condition, or other predictions. In one example, the system 10 includes and AI model 12 utilizing a recurrent neural network for modeling time series by representing the sequence of images into a time series. In further examples, the network architecture for the recurrent neural is modified to process series of images instead of series of points. This is useful for the prediction of disease progression because the disease progression is a temporal process.

As introduced above, the AI model 12 may be trained to generate a prediction. In various embodiments, the prediction may include a set of scores. The model output may be a set of scores where each score is generated by a corresponding node in the output layer. The set of scores may include classification or category scores corresponding to particular category probabilities, such as condition, which may correspond to probability of the presence of a discrete category or a continuous scale value score, for example. The set of scores may be referred to as condition scores. The condition scores may correspond to likelihood of a particular condition or disease of the cornea or anterior segment. Condition scores may correspond to a risk, severity, action, or treatment outcome related to one or more particular conditions or diseases of the cornea or anterior segment. For example, the AI model 12 may associate each output node with a score which can be normalized using a SoftMax layer to give the likelihood of each category. In one embodiment, the set of scores is related to some medical condition. In these or other embodiments, each score may correspond to one or more of a prediction of risk of some future health event, severity of a medical condition, condition progression, an action or treatment, or an outcome of a treatment. In one example, the set of scores includes a set of condition scores wherein at least one of the scores represents a likelihood of a medical condition related to a corneal or anterior segment condition or disease (see, e.g., FIGS. 1G & 1H). In one example, the set of scores includes a corresponding score representing the likelihood of the severity of a corneal or anterior segment condition or disease (see, e.g., FIGS. 1I & 1J). In another example, the set of scores includes a corresponding score representing the likelihood that the patient will develop the corneal or anterior segment disease in the future. In still another example, the set of scores include a corresponding score representing the likelihood that the patient will respond favorably or unfavorably to treatment for the corneal or anterior segment disease. In yet another example, the set of scores includes a corresponding score assisting or guiding a physician decision to utilize a specific treatment technique for the corneal or anterior segment disease. For example, the score may indicate positive or negative treatment techniques or success rates related to techniques applied to eyes having similar features or attributes. In still yet another example, the set of scores include a corresponding score representing the likelihood that the patient's corneal or anterior segment condition will get worse or improve in the future. In various embodiments, the set of scores includes one or more corresponding scores selected from those representing the likelihood of the severity of the corneal or anterior segment condition or disease; representing a severity score of the corneal or anterior segment condition or disease; representing the likelihood that the patient will develop the corneal or anterior segment disease in the future; representing the likelihood that the patient will respond favorably or unfavorably to treatment for the corneal or anterior segment disease; assisting or guiding a physician decision to utilize a specific treatment technique for the corneal or anterior segment disease; or representing the likelihood that the patient's corneal or anterior segment condition will get worse or improve in the future.

In any of the above or other embodiment, the system 10 may include an AI model 12 comprising an ensemble of AI submodels for some model output. Each submodel may generate a similar type of model output, and the system 10 may combine the outputs generated by the ensemble. The AI model 12 output may then be a combined output. In some embodiments, the AI model 12 may converge and/or diverge at one or more model layers, described in more detail below, to form combined or separate submodels for producing specific predictions that may generally be based on classification operations for which the AI model 12 has been trained. The AI model 12 or submodels thereof may output sets of scores. The set of scores may include individual scores corresponding to a discrete categories or value or a continuous scale value score. In some embodiments, each submodel generates an output comprising a set of scores wherein a first set of scores output from a first submodel may result in the AI model 12 selecting particular second submodels for generation of additional output score sets. For example, one or more particular scores in a first set of scores may indicate a high likelihood of a particular disease or condition. The score, input data, or both may then be processed through one or more second submodels trained to generate second sets of scores corresponding to a prediction related to the disease or condition, e.g., risk, severity, action, treatment outcome, or another ancillary prediction. A second set of output scores may include one or more scores that may indicate a likelihood of a particular level or probability of risk, severity, action, treatment outcome, or other ancillary prediction. The second set of scores may similarly direct processing of input data or scores through subsequent submodels.

In various embodiments, input image data may be preprocessed. Preprocessing may be performed by the system 10, e.g., by a preprocessing subsystem 30, or the system 10 may receive preprocessed input image data. For example, the system 10 may be configured to improve image quality of an input image data by de-noising the image and/or removing artifacts. In some embodiments, the system 10 may crop, scale, register, and/or re-center the image. In one embodiment, the AI model 12 may be trained on B-scan or other images wherein multiple scans of the same image cut are provided. For example, using different frames of each cut, and while of the same image, the cuts may include different noise patterns because noise is random. Such training in a noisy environment may make the AI model 12 robust to noise. In some embodiments, any of the AI models 12 described herein, such as those described herein with respect to FIGS. 1A-1J & 4-16, for generating predictions of diagnosis, severity, risk, treatment, and segmentation, may be trained with multiple scans or images of the same cut and/or images that have not been preprocessed to remove certain noise patterns.

Anterior segment OCT images have distinct artifacts that may or may not exist in another OCT image, e.g. specular reflections, and horizontal artifacts. In one embodiment, the accuracy of the AI model 12 is further improved by using preprocessed OCT images and removing those artifacts beforehand.

FIGS. 3A & 3B illustrate a preprocessing operation of an input image. The image shown in FIG. 3A is a raw B-scan image of a cornea and anterior segment that includes vertical and horizontal artifacts. FIG. 3B shows the B-scan image of FIG. 3A after preprocessing by the system 10 to remove artifacts.

In various embodiments, and with continued reference to FIGS. 1A-1J, the system 10 comprises an AI model 12, which may include one or more AI models. The AI model 12 may be any suitable AI model 12. A preferred AI model 12 is a deep learning model comprising a neural network.

Tasks executed by the AI model 12 may include classification, object detection, semantic segmentation, or combinations thereof, for example. Classification may generally include predicting a class or label of images presented to the system 10. On the other hand, object detection may include first finding the label of image then finding a bounding box that contain the object in the image. Semantic segmentation may include utilizing artificial intelligence to find a boundary of detected objects.

In various embodiments, the system 10, or AI model 12 thereof, includes a supervised or unsupervised machine learning process, which may include supervised and unsupervised portions. For example, the AI model 12 may include one or more AI models configured for supervised learning wherein data examples along with associated labels and annotations are used to train the AI model 12—annotation (true output) of the input data to be used during training. In another or further example, the AI model 12 may include one or more AI models configured for unsupervised learning wherein data examples without any labels or annotations are used to train the system 10. In one such example, employing unsupervised learning methods, the AI model 12 is tasked with identifying a natural grouping of the data based on features present in the data. In some examples, the system 10 includes a parametric AI model 12, e.g., a model defined in terms of parameters, and the output may be determined using the input and the parameters. In certain embodiments, the system 10 include a non-parametric AI model 12 that does not need any parameters.

In any of the above or further embodiments, the system 10 may include an AI model 12 that applies multiple layers of processing on the input to obtain the final output. For example, as introduced above, the AI model 12 may employ deep learning models comprising one or more neural networks. Generally speaking, a neural network contains an input layer, hidden layers, and an output layer.

In some embodiments, the system 10 includes an AI model 12 comprising a deep neural network (DNN) that includes an input layer, a plurality of hidden layers, and an output layer. The layers of the network may include nodes or neurons. Nodes of the first hidden layer may be fully connected to the input layer nodes, and the nodes of the last hidden layer may be fully connected to the nodes of the output layer. Input layer nodes may hold the input data and provide the data to connected nodes of the first hidden layer. The input layer nodes do not typically perform calculations or transform the data values of the input data. The output layer may include a classification layer such as one or more SoftMax layers, for example, to perform normalization and/or classification operations. The output layer may include other classification layers in addition to or instead of a SoftMax layer such as classifiers, e.g., binary classifier or regression layer.

In various embodiments, the system 10 includes an AI model 12 comprising a convolutional neural network (CNN). The convolutional neural network may include an input layer, a plurality of hidden layers, and an output layer. The plurality of hidden layers may include one or more convolutional layers, one or more pooling layers, one or more fully connected layers, an output layer comprising one or more classification layers, or combinations thereof.

The CNN may take advantage of the dimensional structure of input data by connecting nodes only to a small region of the input data, which may be selected using the dimensionality of the input data, for example. These regions may be referred to as local receptive fields. Sets of nodes may be referred to as a feature map wherein each node may be connected to a receptive field of nodes below. The feature maps may have shared weights such that each node of a given feature map (which corresponds to the same feature, but shifted across the data dimensions) is constrained to have the same input weights and biases as the other nodes of that feature map. A given layer may have multiple feature maps, each able to correspond to a different feature. Layers containing multiple feature maps are referred to as convolutional layers because the output of a node in the layer is a convolution operation performed on the inputs.

A pooling layer may function to reduce the size of the output of a set of nodes, which is typically the output of a convolutional layer, but pooling layers may be used for any set of nodes, e.g., on top of input nodes. For example, a pooling layer may take the maximum or average activation of a set of nodes as an output, referred to as max-pooling or average pooling. Pooling layers may be applied to each feature map separately. Pooling layers will typically be used between convolutional layers or following a convolutional layer.

A fully connected layer may include one or more fully connected layers. Nodes of the fully connected layer may fully connect to the nodes of the adjacent convolutional or pooling layer. An output layer may include one or more normalization and/or classification layers that may include classifier layers connected to a fully connected layer. In various embodiments, normalization and/or classification layers may include one or more of a SoftMax layer, SVM layer, regression layer, binary classifier layer, output/classier layer, or combination thereof.

In some embodiments, hidden layers may include one or more normalization layers, one or more nonlinear activation layers to increase nonlinearity, such as a ReLU layer, or both. Layers to increase nonlinearity include activation functions and will be associated with layers such as convolutional layers or fully connected layers. Thus, these layers identified herein may include such layers that apply activation functions such as ReLU, TanH, or sigmoid. In various embodiments, nodes of the input layer may be locally connected to a subset of nodes in an adjacent convolutional layer or pooling layer. In some embodiments, one or more fully connected layers may be included between the last pooling or convolutional layer and a classification layer wherein the nodes of the fully connected layer fully connect to the nodes of the adjacent pooling or convolutional layer. In one embodiment, a last fully connected layer fully connects to the one or more nodes of the output layer and the CNN does not include a classification layer. In various embodiments, a last classification layer may output probability scores, or a set of scores, for classes such as conditions, severity, risks, actions, or treatments. In some embodiments, an output layer includes a classifier that applies an activation function such as regression/logical regression, linear, SVM, or SoftMax. A SoftMax layer may provide probabilities for each prediction class for presentation to a further classification layer for output of a prediction. A SoftMax layer may provide normalization operations. In some embodiments, predictions having a threshold probability may be output or probabilities for all or a subset of the possible classes may be output. In some embodiments, an output layer includes a SoftMax layer and a classifier layer such as a binary classifier.

The AI model 12 or output layer thereof may provide predictions utilizing class probability values or scores. For example, a threshold score may indicate a maximum or minimum cut-off with respect to a prediction. In some embodiments, the output layer includes classification or classifier layers for classification of output values or scores with respect to the predictive classes. In some embodiments, the output layer of the AI model 12 may include a binary classifier that is executed to detect which of one or more classes, such as diseases or conditions, to include in the prediction or diagnosis. The AI model 12 may output a prediction of a disease or condition, an ancillary prediction with respect to a disease or condition, or another prediction, for example. In one embodiment, the AI model 12 includes an output layer comprising a SoftMax layer, which in some examples may be referred to as a normalization layer or classification layer. In a further embodiment, an output layer includes a SoftMax layer followed by a classification layer comprising a classifier. A classifier may detect or identify class labels or scores, for example. In one example, the classification layer may include a binary classifier. In one embodiment, the output layer includes a regression layer. A regression layer may be used for continuous output values. A regression layer may follow the last fully connected layer, for example. In one application, an output layer may include more than one separate output layer blocks connected to a single convolutional/pooling layer block.

In some embodiments, the system 10 includes or utilizes an AI model 12 including one or more AI models comprising one or more neural networks, wherein one or more of the neural networks is a CNN, for the classification of corneal diseases. The neural network may include one or more convolutional layers, pooling layers, fully connected layers, or combinations thereof, for example. Convolutional layers may include various depths. Such layers may be stacked to form at least a portion of the network architecture of the neural network. Various architectures may be used. For example, various arrangements of convolutional and pooling layers block may be stacked. Additional layers such as rectifying layers, fully connected layers, an output layer comprising one or more normalization and/or classification layers, or combinations thereof may be used. In some examples, the AI model 12 includes multiple CNNs or portions thereof staked, e.g., vertically or horizontally, or may branch, converge, or diverge. Multiple neural networks may merge or share outputs wherein one or more of the neural networks is a CNN. In one example, an output of a first CNN may be provided as an input or may modify a parameter or weight of a second neural network or vice versa. Some embodiments of the system 10 may analyze outputs of two neural networks to generate a prediction or output that considers at least a portion of the outputs of the first and second neural networks. In some embodiments, the AI model may include classical methods, which may be in addition to deep learning. For example, the AI model may include one or more deep learning submodels and one or more submodels utilizing classical AI methods or classifications.

As introduced above with respect to FIG. 1B, the system 10 may include an analysis subsystem 20. In some embodiments, the analysis subsystem 20 may be configured to collect and/or interpret one or more outputs and translate or transform those outputs in to a more understandable format. For example, the analysis subsystem 10 may collect output class probabilities, associated condition or classification scores, or class labels and associate such probabilities or scores to semantic classifications for presentation to a user. The system 10 may also translate probabilities into confidence scores or other another user friendly format. In one example, the analysis subsystem 10 may include one or more of the above in a health report (see, e.g., FIG. 1B).

In some embodiments, the system 10 includes an AI model 12 comprising a neural network configured to process a sequence of inputs. For example, a recurrent neural network (RNN) may take an input sequence and generate an output sequence. In one embodiment, the system 10 includes an AI model 12 comprising a neural network configured for deep learning according the present disclosure wherein the neural network comprises a joint or hybrid neural network or incorporates outputs of one or more neural networks or layers thereof with one or more additional neural networks or layers thereof, which may include subnetworks. For example, one or more nodes of a convolutional layer, pooling layer, or fully connected layer, which may include a classification layer, of a CNN may connect to one or more nodes of a convolutional layer, pooling layer, fully connected layer, or classification layer of one or more other CNNs or hidden layer of a DNN or RNN.

Figure 4:
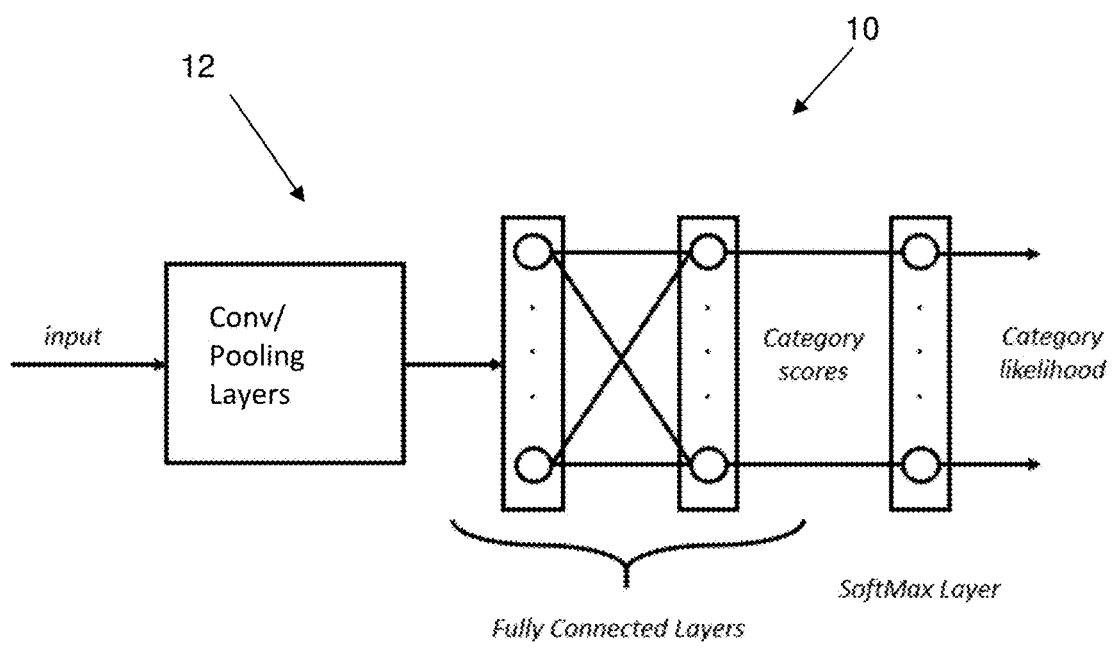
FIG. 4 is a schematic diagram of an embodiment of the system including an AI model for outputting a prediction associated with a cornea or anterior segment of the eye according to various embodiments.

FIG. 4 schematically illustrates a system 10 according to various embodiments. The system 10 includes a more specific implementation of the system 10 for generating predictions related to the cornea or anterior segment of the eye wherein the AI model 12 comprises a CNN. The system 10 includes a neural network comprising a CNN architecture that includes an input layer, a plurality of convolutional and pooling layers, a plurality of fully connected layers, and an outputlayer comprising a SoftMax layer. The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block.

The input data may include an image and/or map such as a B-scan, thickness map, heat map, bullseye map, structural map, and/or other input data described herein. In one embodiment, the CNN may optionally receive and input into the network input data comprising patient data as described above and elsewhere herein (see, e.g., FIGS. 1H, 1J, & 11A-11C).

In the depicted operation, the network takes input data, e.g., an image, and processes it through a set of layers to generate the final output comprising a likelihood for each category or class to which the network is trained. The output may include a set of scores, which in one embodiment may be a single score. The class or category may include cornea or anterior segment diseases or conditions, treatments, severity classes, risk degrees or classes, treatment outcome classes or progression, prognosis, or other network goal or target. More specifically, the input data is processed through a set of convolutional layers and pooling layers, such as max pooling layers. The values or activations (which may be referred to as activation or feature maps) from the last layer of the set of convolutional and pooling layers are passed to a set of fully connected layers for higher level processing, e.g., more global processing related to a classification task. In the final fully connected layer, each node represents a class or category. The network associates each output node with a score, which can be normalized using a classification layer, such as a SoftMax layer in this example, to give the likelihood of each category. In some embodiments, each score may comprise a prediction of a risk of some future health event. Only outer nodes and connections are illustrated, but the fully connected and classification layer may include additional nodes. Nodes are not illustrated for the convolution and pooling layers; however, these layers will typically include much larger numbers of nodes than fully connected layers. In some embodiments, the AI model 12 may be further configured to provide augmented predictions from a single model prediction. For example, as described in more detail below, the AI model 12 may include a model that outputs a disease prediction and one or more additional predictions, which may be related to the disease prediction, such as one or more of risk, severity, risk, progression, action, treatment, or prognosis.

In a further embodiment, the system 10 may also include an analysis subsystem as described above with respect to FIG. 1B configured to generate health analysis data using the set of scores and present the data to the user in a health report. The system 10 may also include a database for storing output data. The database may also store historical outputs from which the analysis module may utilize in preparation of the health report, e.g., for comparison purposes or to identify an improved or worsening condition.

Figure 5:
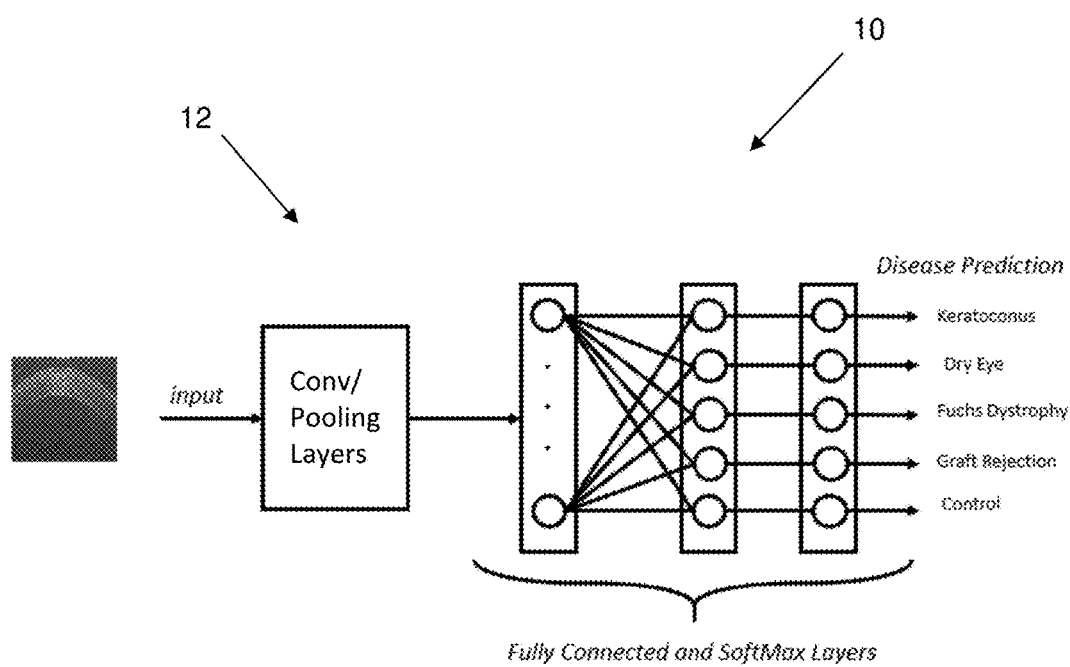
FIG. 5 is a schematic diagram of an embodiment of the system including an AI model for predicting a condition or disease of the cornea or anterior segment of the eye according to various embodiments.

FIG. 5 schematically illustrates an embodiment of the system 10 according to various embodiments. The system 10 includes a more specific implementation of the system 10 as shown in FIG. 1G for predicting a condition or disease of the cornea or anterior segment of the eye wherein the AI model 12 comprises a CNN. The AI model 12 is trained to receive the input image and process it to generate a model output. In operation, the AI model 12 may process input data comprising one or more B-scans. In a further embodiment, the CNN may optionally receive and input into the network input data comprising patient data as described above and elsewhere herein (see, e.g., FIGS. 1H, 1J, & 11A-11C). In some embodiments, input data may include other input data such as thickness maps, heat maps, bullseye maps, structure map, and/or other input data described herein in addition to or instead of images such as B-scan images.

The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. Thus, various embodiments may combine aspects from different AI modeling methodologies with one or more convolutional neural network bases comprising convolutional/pooling layer blocks (cony/pooling layers). It will be appreciated that cony/pooling layer blocks in any embodiment described herein may include other layers therebetween or prior to the fully connected layer block such as one or more ReLU layer.

The output layer of the AI model 12 receives the output generated by the last fully connected layer and generates the model output. The model output may include a set of scores wherein each score is generated by a corresponding node in the output layer. The set of scores include condition scores. Generally, the set of condition scores are specific to a medical condition that the AI model 12 has been trained to predict, such as a disease of the cornea or anterior segment of the eye. For example, the AI model 12 output in FIG. 5 is specific to a medical condition, such as a disease, represented by the nodes of the final fully connected layer and the nodes of the output layer, which in this embodiment includes a SoftMax layer. More specifically, the AI model 12 has been trained to predict corneal or anterior segment diseases: keratoconus, dry eye, Fuchs dystrophy, graft rejection episode or failure, and glaucoma.

The AI model 12 may be trained to predict multiple medical conditions and multiple combinations of those medical conditions. For example, in one embodiment, the set of condition scores may represent the likelihood that the patient has some corneal or anterior segment condition selected from corneal ectasia (such as keratoconus), keratoplasty graft rejection episode and failure, corneal graft rejection, aqueous deficiency and evaporative dry eye syndrome (DES), Fuchs' dystrophy, corneal limbal stem cell deficiency, cataract, or glaucoma. In other embodiments, each score may comprise a prediction of a risk of some future health event.

Thus, the AI model 12 may be configured to provide multiple diagnoses, such as up to two diagnoses, for the same eye, if a second diagnosis is present. For example, the probability of a diagnosis is calculated and if a second diagnosis has a probability above a threshold then that second diagnosis may also be provided. In some embodiments, the output layer of the AI model 12 may include a binary classifier that is executed to detect which of one or more classes, such as diseases or conditions, to include in the prediction or diagnosis. For example, the diagnosis could be keratoconus with dry eye. In some embodiments, the AI model 12 may be configured to provide more than two diagnoses when present.

In some embodiments, the AI model 12 may be further configured to provide augmented predictions from a single model prediction. For example, as described in more detail below, the AI model 12 may include a model that outputs a disease prediction and one or more additional predictions, which may be related to the disease prediction, such as one or more of risk, severity, risk, progression, action, treatment, or prognosis.

As introduced above, the system 10 may be configured to include an AI model 12 having an efficient design. The AI model 12, for example, may include simple categories, such as single prediction member, and/or compound or complex categories that include multiple prediction members in a single category, e.g., augmented categories. In one example, in the training of the AI model 12, a category that represents cases which have multiple conditions or diseases as a separate case may be added. For example, the AI model 12 may include members that overlap with those in a single member category, such as in the example above. In other embodiments, there may be no member overlap. In one example, all categories are compound or complex. Thus, the system 10 may introduce the concept of simple categories and compound, complex, or augmented categories.

Figure 9:
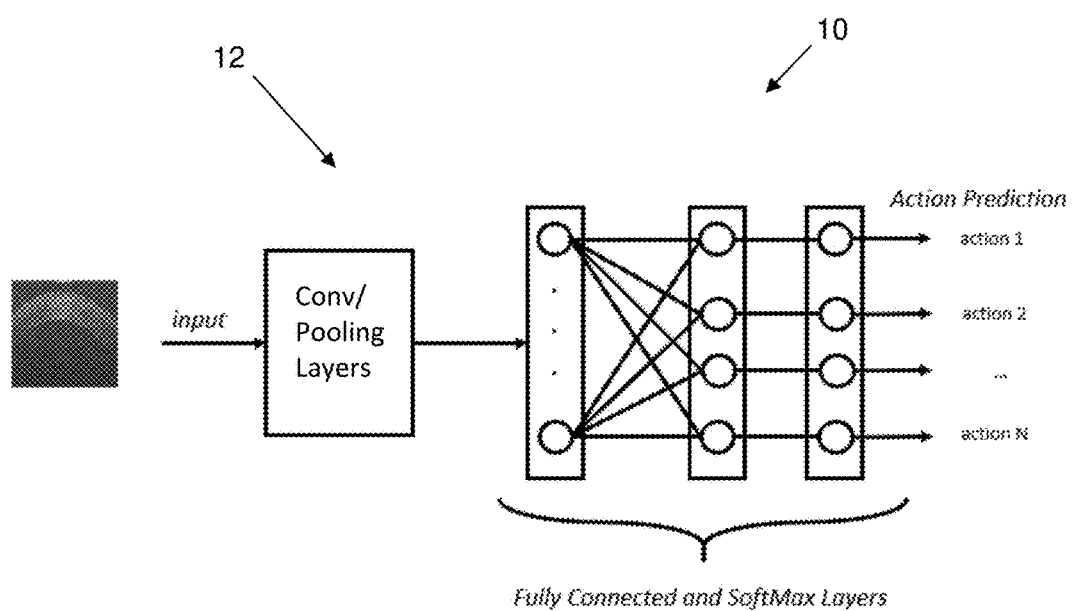
FIG. 9 is a schematic diagram of an embodiment of the system including an AI model for outputting an action prediction with respect to a condition or disease of the cornea or anterior segment of the eye according to various embodiments.
Figure 10:
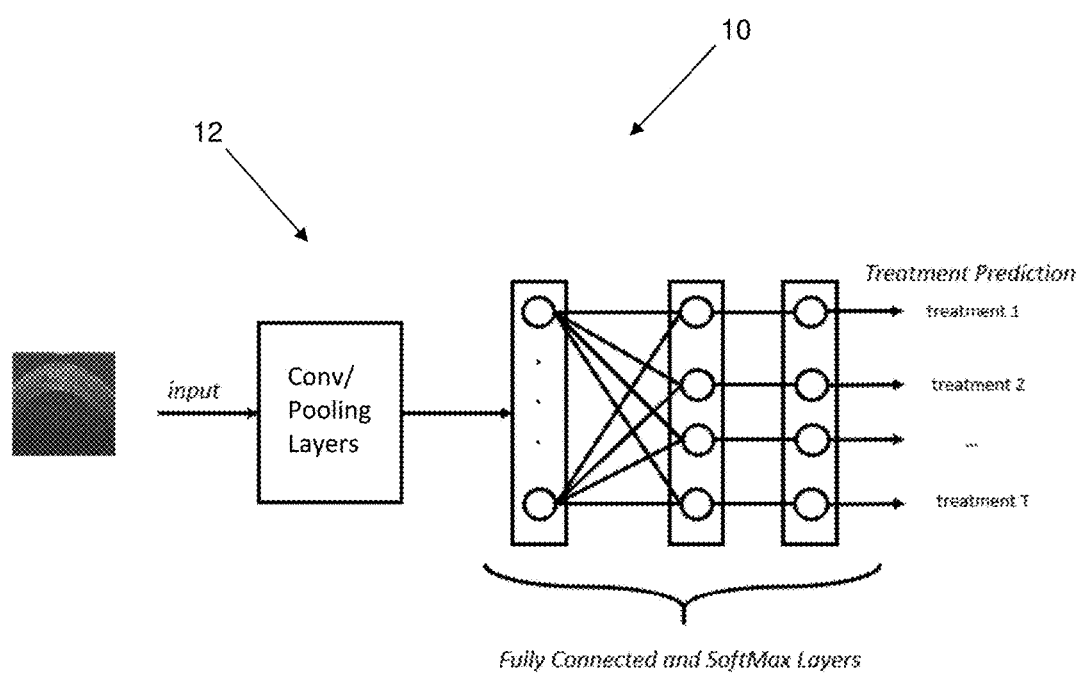
FIG. 10 is a schematic diagram of an embodiment of the system including an AI model for outputting a treatment prediction with respect to a condition or disease of the cornea or anterior segment of the eye according to various embodiments.

In a further embodiment, the set of condition scores includes one or more corresponding scores selected from those representing the likelihood of the severity of the corneal or anterior segment condition or disease (see, e.g., FIG. 6); representing a severity score of the corneal or anterior segment condition or disease (see, e.g., FIG. 7); representing the likelihood that the patient will develop the corneal or anterior segment disease in the future (see, e.g., FIG. 8); representing the likelihood that the patient will respond favorably or unfavorably to treatment for the corneal or anterior segment disease (see, e.g., FIG. 9); assisting or guiding a physician decision to utilize a specific treatment technique for the corneal or anterior segment disease; or representing the likelihood that the patient's corneal or anterior segment condition will get worse or improve in the future (see, e.g., FIG. 10).

In a further embodiment, the system 10 described with respect to FIG. 5 may also include an analysis subsystem as described above with respect to FIG. 1B configured to generate health analysis data using the set of scores and present the data to the user in a health report. The system 10 may also include a database for storing output data. The database may also store historical outputs from which the analysis module may utilize in preparation of the health report, e.g., for comparison purposes or to identify an improved or worsening condition.

Figure 6:
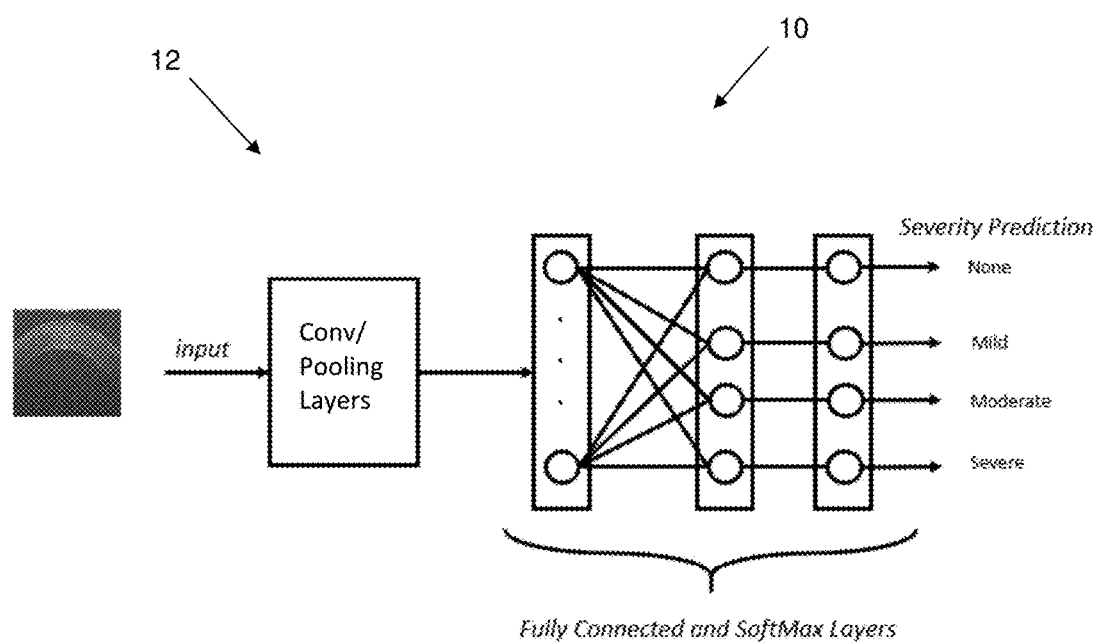
FIG. 6 is a schematic diagram of an embodiment of the system including an AI model for predicting a severity of a condition or disease of the cornea or anterior segment of the eye according to various embodiments.

FIG. 6 schematically illustrates an embodiment of the system 10 according to various embodiments. The system 10 includes a more specific implementation of the system 10 as shown in FIG. 1I for predicting a severity of a condition or disease of the cornea or anterior segment of the eye wherein the AI model 12 comprises a CNN.

The AI model 12 is trained to receive the input image and process it to generate a model output. In operation, the AI model 12 may process input data comprising one or more B-scans. In a further embodiment, the AI model 12 may optionally receive and input into the network input data comprising patient data as described above and elsewhere herein (see, e.g., FIGS. 1H, 1J, & 11A-11C). In some embodiments, input data may include other input data such as thickness maps, heat maps, bullseye maps, structure map, and/or other input data described herein in addition to or instead of images such as B-scan images.

The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. The output layer of the AI model 12 receives the output generated by the last fully connected layer and generates the model output. Generally, the AI model 12 has been trained to predict a level of severity for one or more particular conditions or diseases of the cornea or anterior segment of the eye. The model output may include a discrete value or category corresponding to the level of severity of a cornea or anterior segment condition or disease.

The AI model 12 illustrated in FIG. 6 may predict the likelihood that the patient's cornea has some medical condition and predict the condition level. The AI model 12 may include simple categories, such as single prediction member, and/or compound or complex categories that include multiple prediction members in a single category, e.g., augmented categories. In one example, the predictions may be made through separate AI models. For example, after making an initial prediction identifying a condition, for example as described with respect to FIG. 5, the system 10 may process the input data through a second AI model 12, e.g., CNN, specific to the condition identified to generate a predicted severity. In another example, the predictions may be made through a single AI model 12 comprising a CNN wherein the probability score is used to correlate a severity. For example, a first threshold probability may lead to a predicted condition and additional thresholds in the probability score may be set to indicate severity as the probability score increases. In a further example, a first output node outputs to a second output node, such as when the output value is above a predefined threshold. The second output node may be specific to a condition implicated by the threshold value. In one embodiment, the second output node applies a weighted algorithm to the output value to determine a severity level of a condition. In another example, the predictions may be made in a joint CNN or a CNN that diverges or converges. For example, the AI model 12 may include separate sets of fully connected layers that fully connect to common convoluted, pooling, or fully connected layers. In a further example, the CNN may include additional convoluted and pooling layers after diverging into separate fully connected layers. The CNN may therefore include multiple sets of fully connected and output layers configured to perform separate classification tasks from the same initial input data diverted along separate processing paths. Multiple networks or submodels may similarly be combined or converged into one network. In some embodiments, converging, diverging or combined networks may be trained jointly. For example, training may include defining a global loss function (e.g., error function) based on an output of the individual networks and tuning the networks accordingly.

In a further embodiment, the system 10 described with respect to FIG. 6 may also include an analysis subsystem as described above with respect to FIG. 1B configured to generate health analysis data using the set of scores and present the data to the user in a health report. The system 10 may also include a database for storing output data. The database may also store historical outputs from which the analysis subsystem may utilize in preparation of the health report, e.g., for comparison purposes or to identify an improved or worsening condition. In one embodiment, the analysis module generates health analysis data from condition scores. Using the health analysis data and knowing predicted likelihood of some medical condition, the analysis subsystem may predict the level of severity as a condition level. In one example, the analysis subsystem utilizes the probability score to correlate a severity level, such as increasing a severity level corresponding to a probability of the condition above a threshold probability. In a further example, the analysis subsystem analyzes probability scores and applies a weighted algorithm to determine a severity level.

In some embodiments, the system 10 described with respect to FIG. 6 may further include or operatively communicate with a preprocessing subsystem (see, e.g., FIG. 1E) to preprocess image data or request and/or receive preprocessed image data, for example, as described above with respect to FIGS. 3A & 3B and accompanying discussion. In the above or a different embodiment, the system 10 may include or associate with a map generator or a preprocessing subsystem comprising a map generator, for example, as described above with respect to FIG. 1E and accompanying discussion to receive or generate maps, see e.g., FIGS. 2B & 2C. In any of the above or another embodiment, the system 10 may include or be configured to operatively communicate with an OCT imaging system or OCT image library to obtain image data, for example, as described above with respect to FIGS. 1C & 1D and accompanying discussions.

Figure 7:
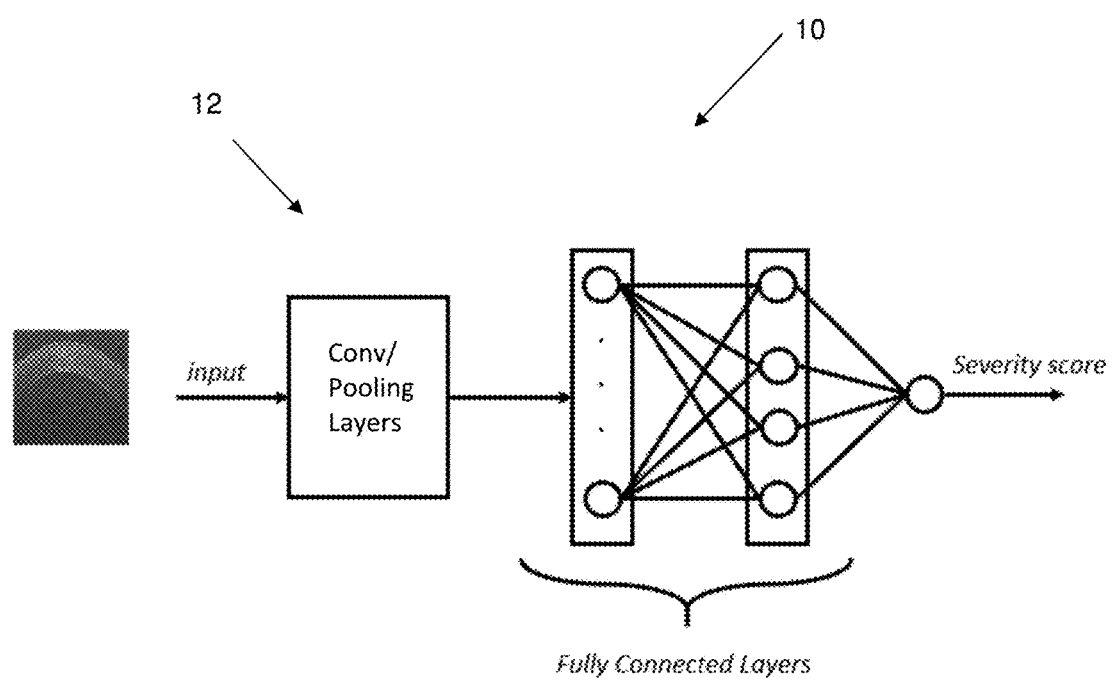
FIG. 7 is a schematic diagram of an embodiment of the system including an AI model for predicting a severity score with respect to a condition or disease of the cornea or anterior segment of the eye according to various embodiments.

FIG. 7 schematically illustrates an embodiment of the system 10 according to various embodiments. The system 10 includes a more specific implementation of the system 10 as shown in FIG. 1I for predicting a severity score of a condition or disease of the cornea or anterior segment of the eye wherein the AI model 12 comprises a CNN. Thus, in contrast to the AI model 12 shown in FIG. 6 that predicts a level of severity of a medical condition, the AI model 12 is trained to represent severity by a score instead of a discrete value. This may be useful when a continuous scale value is wanted from the system 10.

The AI model 12 is trained to receive the input image and process it to generate a model output. In operation, the AI model 12 may process input data comprising one or more B-scans. In a further embodiment, the AI model 12 may optionally receive and input into the network input data comprising patient data as described above and elsewhere herein (see, e.g., FIGS. 1H, 1J, & 11A-11C). In a further or other embodiments, input data may include other input data such as thickness maps, heat maps, bullseye maps, structure maps, and/or other input data described herein in addition to or instead of images such as B-scan images.

The AI model 12 may include various arrangements of convolutional layers, pooling layers, fully connected layers, normalization layers, as well as other layers. In the illustrated embodiment, the AI model 12 includes a set of convoluted and pooling layers followed by a set of fully connected layers, and an output layer. Generally, the AI model 12 has been trained to predict a severity for one or more particular conditions or diseases of the cornea or anterior segment of the eye. In operation, the input layer receives the data input, which is then processed through the convolutional and pooling layers before the processing is passed to the fully connected layers. After being processed through the fully connected layers, the node of the output layer receives the output activation values generated by the nodes of last fully connected layer. The output layer may comprise an output node that then processes the activation values to generate a model output comprising a severity score, which is a continuous score corresponding to the level of severity of the patient's cornea. The output layer may comprise a regression layer comprising the output node. In some embodiments, the output layer may comprise a normalization layer to conform an activation value to an output score in a desired range. In one embodiment, the output layer comprises a SoftMax layer configured to normalize one or a combination of the activation values to calculate a normalized output score comprising the prediction score.

The AI model 12 illustrated in FIG. 7 may be configured similar to that described above with respect to FIG. 6. For example, the AI model 12 may predict the likelihood that the patient's cornea has some medical condition and predict the severity score. The AI model 12 may include an integrated model including one or more networks or submodels, which may be separate, joint, converged, diverged, or combined, for example, to generate one or more predictions within one or more categories or classes of categories. The AI model 12 may include simple categories, such as single prediction member, and/or compound or complex categories that include multiple prediction members in a single category, e.g., augmented categories, as described herein.

In a further embodiment, the system 10 described with respect to FIG. 7 may also include an analysis subsystem as described above with respect to FIG. 1B configured to generate health analysis data using the set of scores and present the data to the user in a health report. The system 10 may also include a database for storing output data. The database may also store historical outputs from which the analysis subsystem may utilize in preparation of the health report, e.g., for comparison purposes or to identify an improved or worsening condition. Using the health analysis data and knowing predicted likelihood of one or more medical conditions, the analysis subsystem may generate a predicted severity score for one or more medical conditions, such as those having a predicted likelihood above a predetermined threshold. In one example, the analysis subsystem utilizes the probability score to correlate a severity score, such as increasing a severity score corresponding to a probability of the condition above a threshold probability. In a further example, the analysis subsystem analyzes probability scores and applies a weighted algorithm to determine a severity score.

In some embodiments, the system 10 described with respect to FIG. 7 may further include or operatively communicate with a preprocessing subsystem (see, e.g., FIG. 1E) to preprocess image data or request and/or receive preprocessed image data, for example, as described above with respect to FIGS. 3A & 3B and accompanying discussion. In the above or a different embodiment, the system 10 may include or associate with a map generator or a preprocessing subsystem comprising a map generator or a preprocessing subsystem comprising a map generator, for example, as described above with respect to FIG. 1E and accompanying discussion to receive or generate maps, see e.g., FIGS. 2B & 2C. In any of the above or another embodiment, the system 10 may include or be configured to operatively communicate with an OCT imaging system or OCT image library to obtain image data, for example, as described above with respect to FIGS. 1C & 1D and accompanying discussions.

Figure 8:
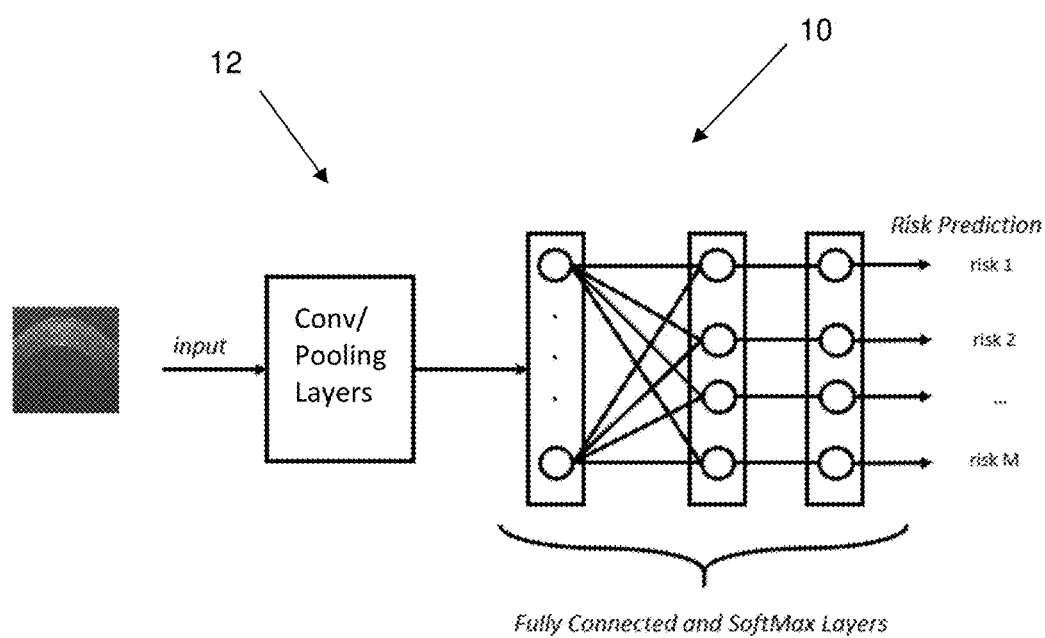
FIG. 8 is a schematic diagram of an embodiment of the system including an AI model for outputting a risk prediction with respect to a condition or disease of the cornea or anterior segment of the eye according to various embodiments.

FIG. 8 schematically illustrates an embodiment of the system 10 according to various embodiments. The system 10 includes an AI model 12 trained to output a risk prediction, such as a prediction of the progression of a cornea or anterior segment condition. The AI model 12 is configured to output a discrete value or category corresponding to the predicted risk for a patient's cornea. In one example, the AI model 12 configured to output risk predictions with respect to keratoconus may include values representing a patient's risk or likelihood of having a progressive course or stable course. In another example, the AI model 12 configured to output risk predictions with respect to Fuchs dystrophy may include categories or values representing a patient's risk or likelihood of corneal decompensation after cataract surgery. In yet another example, the AI model configured to output risk predictions with respect to graft rejection may include categories or values representing a patient's risk or likelihood of a reversal response through steroid treatment.

The AI model 12 is trained to receive the input image and process it to generate a model output. In operation, the AI model 12 may process input data comprising one or more B-scans. In a further embodiment, the AI model 12 may optionally receive and input into the network input data comprising patient data as described above and elsewhere herein (see, e.g., FIGS. 1H, 1J, & 11A-11C). In one embodiment, input data may include other input data such as thickness maps, heat maps, bullseye maps, structure maps, and/or other input data described herein in addition to or instead of images such as B-scan images.

The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. Generally, the AI model 12 has been trained to predict a risk of progression for one or more particular conditions or diseases of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of last fully connected layer. The output nodes then process the activation values to generate a model output comprising a risk prediction.

The AI model 12 illustrated in FIG. 8 may be configured similar to that described above with respect to FIGS. 6 & 7. For example, the AI model 12 may predict the likelihood that the patient's cornea has some medical condition and predict an associated risk. The AI model 12 may include an integrated model including one or more networks or submodels, which may be separate, joint, converged, diverged, or combined, for example, to generate one or more predictions within one or more categories or classes of categories. In one embodiment, the AI model 12 generates a set of scores is specific to a particular cornea or anterior segment condition or disease. The set of scores may comprise a set of risk scores, each risk score specific to a risk level with respect to progression of the particular cornea or anterior segment condition or disease to which the set of scores is specific. In a further example, the output prediction may be a discrete value or category corresponding to a predicted risk level.

In a further embodiment, the system 10 described with respect to FIG. 8 may further include or operatively communicate with an analysis subsystem, as described above with respect to FIG. 1B, configured to generate health analysis data using the set of scores and present the data to the user in a health report. The system 10 may also include a database for storing output data. The database may also store historical outputs from which the analysis subsystem may utilize in preparation of the health report, e.g., for comparison purposes or to identify an improved or worsening condition. In one embodiment, the analysis module generates health analysis data from condition scores. Using the health analysis data and knowing predicted likelihood of one or more medical conditions, the analysis subsystem may generate a predicted risk for one or more medical conditions, such as those having a predicted likelihood above a predetermined threshold. In one example, the analysis subsystem utilizes the probability score to correlate a discrete risk value or category, such as increasing a risk category corresponding to a probability of the condition above a threshold probability. In a further example, the analysis subsystem analyzes probability scores and applies a weighted algorithm to determine a predicted risk.

In some embodiments, the system 10 described with respect to FIG. 8 may further include or operatively communicate with a preprocessing subsystem (see, e.g., FIG. 1E) to preprocess image data or request and/or receive preprocessed image data, for example, as described above with respect to FIGS. 3A & 3B and accompanying discussion. In the above or a different embodiment, the system 10 may include or associate with a map generator or a preprocessing subsystem comprising a map generator, for example, as described above with respect to FIG. 1E and accompanying discussion to receive or generate maps, see e.g., FIGS. 2B & 2C. In any of the above or another embodiment, the system 10 may include or be configured to operatively communicate with an OCT imaging system or OCT image library to obtain image data, for example, as described above with respect to FIGS. 1C & 1D and accompanying discussions.

FIG. 9 schematically illustrates an embodiment of the system 10 according to various embodiments. The system 10 includes an AI model 12 trained to output an action, such as a prediction of an action to be taken with respect to the patient's cornea or anterior segment. The AI model 12 is configured to output a discrete value or category corresponding to the predicted action. In one example, the AI model 12 is configured to output a prediction with respect to dry eye and includes categories or values representing a patient's likelihood of responding to just use of artificial tears, use of steroids, or use of autologous serum tears. The AI model 12 may also present the treatment option that would work best according to the historical data it was trained on. In another example, the AI model 12 is configured to output a prediction with respect to keratoconus eyes and includes categories or values representing a patient's likelihood of responding or requiring cross linking treatment, e.g., because the disease is progressing, while others may have a stationary disease and only need to be observed. Some may have scaring and need keratoplasty. Some patients may improve with contact lens while others will not. The AI model 12 may therefore output the best course of action.

The AI model 12 is trained to receive the input image and process it to generate a model output. In operation, the AI model 12 may process input data comprising one or more B-scans. In a further embodiment, the AI model 12 may optionally receive and input into the network input data comprising patient data as described above and elsewhere herein (see, e.g., FIGS. 1H, 1J, & 11A-11C). In embodiments, input data may include other input data such as thickness maps, heat maps, bullseye maps, structure maps, and/or other input data described herein in addition to or instead of images such as B-scan images.

The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. Generally, the AI model 12 has been trained to predict an action to be taken with respect to the patient's cornea or anterior segment that relates to one or more particular conditions or diseases of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of last fully connected layer. The output nodes then process the activation values to generate a model output comprising an action prediction.

The AI model 12 illustrated in FIG. 9 may be configured similar to that described above with respect to FIGS. 6 & 7. For example, the AI model 12 may predict the likelihood that the patient's cornea has some medical condition and predict an associated risk. The AI model 12 may include an integrated model including one or more networks or sub-models, which may be separate, joint, converged, diverged, or combined, for example, to generate one or more predictions within one or more categories or classes of categories. In one embodiment, the AI model 12 generates a set of scores is specific to a particular cornea or anterior segment condition or disease. The set of scores may include a set of action scores, each action score specific to a particular action with respect to the particular cornea or anterior segment condition or disease to which the set of scores is specific. In a further example, AI model 12 may output a prediction comprising a discrete value or category corresponding to a predicted action. The AI model 12 may include simple categories, such as single prediction member, and/or compound or complex categories that include multiple prediction members in a single category, e.g., augmented categories, as described herein.

In a further embodiment, the system 10 described with respect to FIG. 9 may also include an analysis subsystem as described above with respect to FIG. 1B configured to generate health analysis data using the set of scores and present the data to the user in a health report. The system 10 may also include a database for storing output data. The database may also store historical outputs from which the analysis subsystem may utilize in preparation of the health report, e.g., for comparison purposes or to identify an improved or worsening condition. In one embodiment, the analysis module generates health analysis data from condition scores. Using the health analysis data and knowing predicted likelihood of one or more medical conditions, the analysis subsystem may generate a predicted action for one or more medical conditions, such as those having a predicted likelihood above a predetermined threshold. In one example, the analysis subsystem utilizes the probability score to correlate a discrete value or category for an action. In a further example, the analysis subsystem analyzes probability scores and applies a weighted algorithm to determine a predicted action.

In some embodiments, the system 10 described with respect to FIG. 9 may further include or operatively communicate with a preprocessing subsystem (see, e.g., FIG. 1E) to preprocess image data or request and/or receive preprocessed image data, for example, as described above with respect to FIGS. 3A & 3B and accompanying discussion. In the above or a different embodiment, the system 10 may include or associate with a map generator or a preprocessing subsystem comprising a map generator, for example, as described above with respect to FIG. 1E and accompanying discussion to receive or generate maps, see e.g., FIGS. 2B & 2C. In any of the above or another embodiment, the system 10 may include or be configured to operatively communicate with an OCT imaging system or OCT image library to obtain image data, for example, as described above with respect to FIGS. 1C & 1D and accompanying discussions.

FIG. 10 schematically illustrates an embodiment of the system 10 according to various embodiments. The system 10 includes an AI model 12 trained to output an action, such as a prediction of treatment to be taken with respect to the patient's cornea or anterior segment. The AI model 12 is configured to output a discrete value or category corresponding to the predicted treatment.

The AI model 12 is trained to receive the input image and process it to generate a model output. In operation, the AI model 12 may process input data comprising one or more B-scans. In a further embodiment, the AI model 12 may optionally receive and input into the network input data comprising patient data as described above and elsewhere herein (see, e.g., FIGS. 1H, 1J, & 11A-11C). In some embodiments, input data may include other input data such as thickness maps, heat maps, bullseye maps, structure maps, and/or other input data described herein in addition to or instead of images such as B-scan images.

The AI model 12 may include various arrangements of convolutional layers, pooling layers, fully connected layers, an output layer comprising one or more normalization layers and/or classification layers, which may include a regression layer, as well as other layers. In the illustrated embodiment, the AI model 12 includes a set of convoluted and pooling layers followed by a set of fully connected layers, and an output layer. The output layer includes a normalization and/or classification layer, which includes a SoftMax layer in the illustrated embodiment. In one embodiment, the classification layer includes a classical classifier such as a discriminant analysis or support vector machine (SVM). In some embodiments, the output layer may further include instead or in addition to an SVM or SoftMax, a classifier layer comprising a binary classifier. After converting an image into a set of features through convolutional layers, these features may be used with other classifiers which may be part of the same or a different output layer block. Generally, the AI model 12 has been trained to predict a treatment to be taken with respect to the patient's cornea or anterior segment that relates to one or more particular conditions or diseases of the cornea or anterior segment of the eye. In operation, the input layer receives the data input, which is then processed through the convolutional and pooling layers before the processing is passed to the fully connected layers. After being processed through the fully connected layers, the nodes of the output layer receive the output activation values generated by the nodes of last fully connected layer. The output nodes then process the activation values to generate a model output comprising a treatment prediction.

The AI model 12 illustrated in FIG. 10 may be configured similar to that described above with respect to FIGS. 6 & 7. For example, the AI model 12 may predict the likelihood that the patient's cornea has some medical condition and predict an associated risk. The AI model 12 may include separate, joint/diverged, or combined AI model 12 networks, for example. In one embodiment, the AI model 12 generates a set of scores specific to a particular cornea or anterior segment condition or disease. The set of scores may comprise a set of treatment scores, each treatment score specific to a particular treatment with respect to the particular cornea or anterior segment condition or disease to which the set of scores is specific. In one example, the AI model 12 outputs a prediction comprising a discrete value or category corresponding to at least one of the treatments. The AI model 12 may include simple categories, such as single prediction member, and/or compound or complex categories that include multiple prediction members in a single category, e.g., augmented categories, as described herein.

In a further embodiment, the system 10 described with respect to FIG. 10 may also include an analysis subsystem as described above with respect to FIG. 1B configured to generate health analysis data using the set of scores and present the data to the user in a health report. The system 10 may also include a database for storing output data. The database may also store historical outputs from which the analysis subsystem may utilize in preparation of the health report, e.g., for comparison purposes or to identify an improved or worsening condition. In one embodiment, the analysis module generates health analysis data from condition scores. Using the health analysis data and knowing predicted likelihood of one or more medical conditions, the analysis subsystem may generate a predicted treatment for one or more medical conditions, such as those having a predicted likelihood above a predetermined threshold. In one example, the analysis subsystem utilizes the probability score to correlate a discrete value or category for a treatment. In a further example, the analysis subsystem analyzes probability scores and applies a weighted algorithm to determine a predicted treatment.

In some embodiments, the system 10 described with respect to FIG. 10 may further include or operatively communicate with a preprocessing subsystem (see, e.g., FIG. 1E) to preprocess image data or request and/or receive preprocessed image data, for example, as described above with respect to FIGS. 3A & 3B and accompanying discussion. In the above or a different embodiment, the system 10 may include or associate with a map generator or a preprocessing subsystem comprising a map generator, for example, as described above with respect to FIG. 1E and accompanying discussion to receive or generate maps, see e.g., FIGS. 2B & 2C. In any of the above or another embodiment, the system 10 may include or be configured to operatively communicate with an OCT imaging system or OCT image library to obtain image data, for example, as described above with respect to FIGS. 1C & 1D and accompanying discussions.

It will be appreciated that multiple predictions may be made utilizing one or more networks. Multiple sets of scores may be generated. The sets of scores may be specific to particular conditions or diseases. A single model may generate multiple sets of scores. As noted elsewhere, scores and predictions may be generated by an ensemble of networks. The networks may be integrated, e.g., sharing input or output data or having combined combinations of network layers. It will also be appreciated that the system 10 may include an AI model 12 comprising multiple AI networks or models, e.g., submodels, as described above and elsewhere herein. For example, the AI model 12 may include a submodel for generating a disease prediction and one or more submodels for generating ancillary predictions corresponding to the disease prediction (e.g., severity, risk, action, treatment, progression). In various embodiments, the AI model 12 may comprise a network architecture as described herein with respect to FIGS. 18-14 or elsewhere herein. In various embodiments, the AI model 12 described with respect to FIGS. 1A-1J, FIG. 4, or FIG. 5 includes multiple submodels including two or more of the AI models 12 described with respect to FIGS. 6-10. In some such embodiments, the AI model 12 may include multiple submodels of one or more of the AI models 12 described with respect to FIGS. 6-10. In various embodiments, any of the above AI models 12 may include (e.g., integrate or operatively combine with, which may include an analysis subsystem including important region predictions in a health report) the AI subsystem 12 described with respect to FIGS. 12-13. Similarly, any of the above AI models 12 may incorporate patient data, such as demographic data, as described with respect to FIG. 11A-11C. Any of the above embodiments, may also take as input any input data described herein, including FIGS. 2A-3B.

Figure 11A:
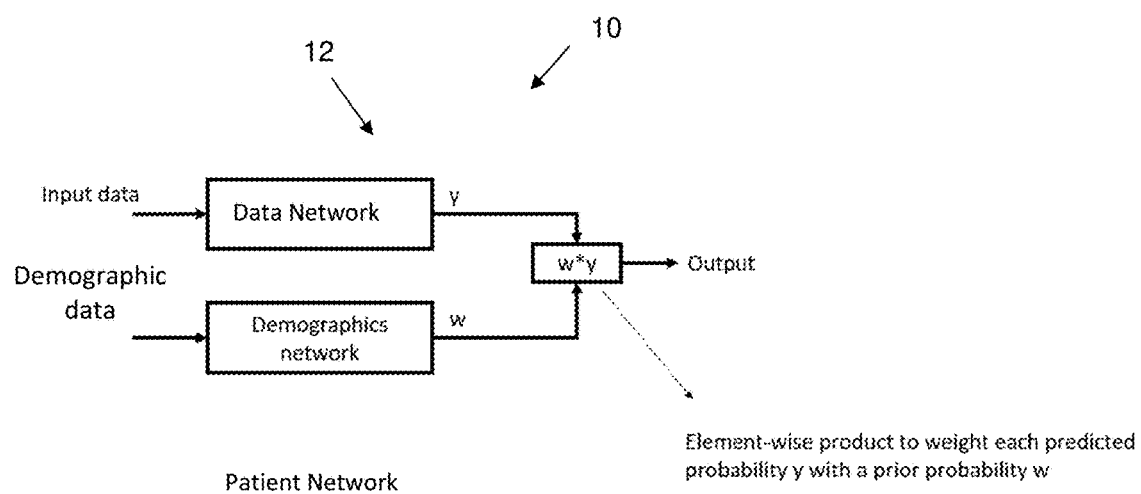
FIGS. 11A-11C is a schematic diagram of embodiments of the system that include augmentation of an AI model with patient data according to various embodiments.
Figure 11B:
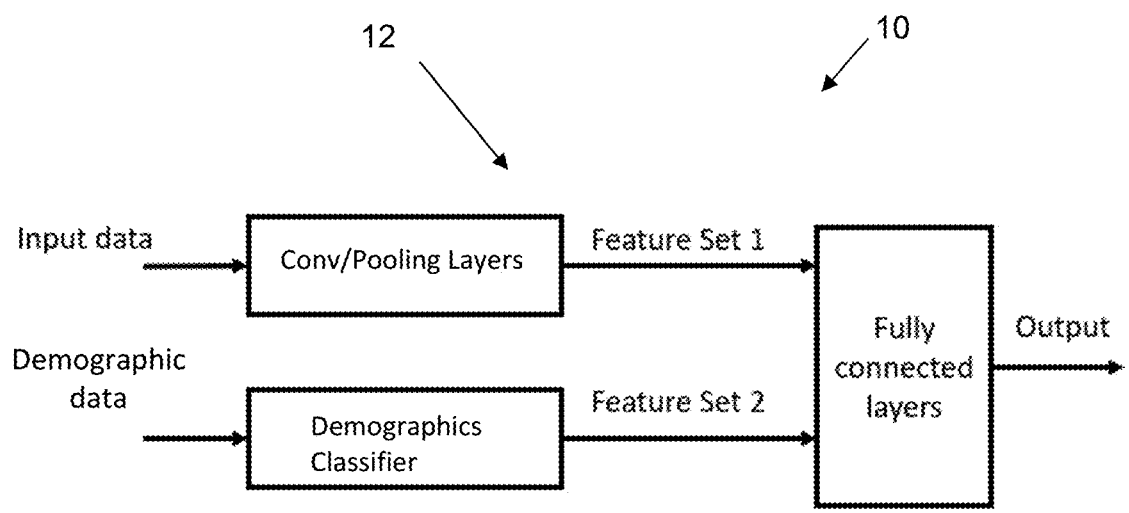
Figure 11C:
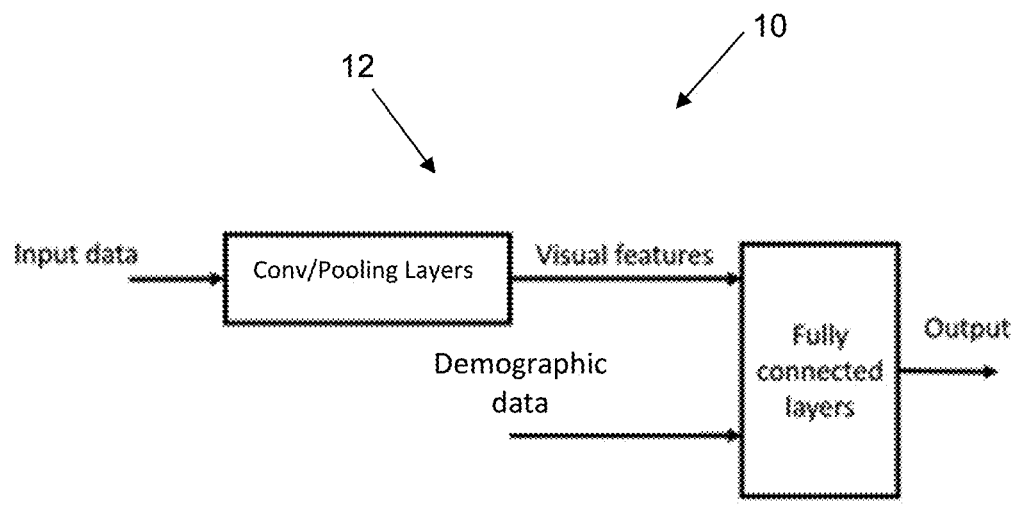

FIGS. 11A-11C schematically illustrates embodiments of the system 10 that include augmentation of the AI model 12 with patient data according to various embodiments. Such an AI model 12 may be implemented with or may be included in AI model 12 described with respect to FIGS. 1H & 1J. The patient data may include any type of patient data, such as demographic data or medical data. The AI model 12 has been trained and tuned to process input data to generate a desired output prediction, such as a category likelihood (see, e.g., FIG. 4), a disease prediction (see, e.g., FIG. 5), a severity prediction (see, e.g., FIG. 6), a severity score (see, e.g., FIG. 7), a risk prediction (see, e.g., FIG. 8), an action prediction (see, e.g., FIG. 9), or a treatment prediction (see, e.g., FIG. 10), for example. The input data may include images such as B-scans, color images, thickness maps, heat maps, bullseye maps, structure maps, and/or other input data described herein.

With particular reference to FIG. 11A, in various embodiments, patient data may be incorporated via a demographics network. The demographic network may comprise an AI model 12 such as a Bayesian Model. In another embodiment, the demographics network includes is a part of an AI model 12 comprising a neural network trained on patient data. In one example, such a neural network may be trained on patient data only. In some embodiments, the demographic network may be implemented as a shallow neural network consisting of fully connected layers only. In one embodiment, the demographics network comprises an AI model 12 or submodel thereof utilizing classical machine learning, such as Support Vector Machines (SVM) or Discriminant Analysis. As shown in FIG. 11A, the demographic network is configured to receive input data comprising patient data or demographic data and to generate output weights w with respect to one, more, or all y outputs. The final output, which may be generated by a combined output layer for both networks or by an analysis subsystem, as described herein, may be determined by calculating an element-wise product to weight each prediction value y with a prediction value w determined from the patient network taking as input data the patient related data. In the illustrated embodiment, the y output comprises a predicted probability based on image data, thickness maps, heat maps, structure maps, and/or bullseye maps and output y from the patient network comprises a prior probability.

With particular reference to FIG. 11B, the system 10 may include an AI model 12 implementation that incorporates patient data comprising demographic data using a demographic classifier output as additional features to the fully connected layers of the CNN or extension thereof. FIG. 11B illustrates an example, of a converging network that shares a fully connected layer block. The demographic classifier is configured to receive input data comprising demographic data, process the input data, and output feature set 2, which may be a set of activation values generated by the processing of demographics input data. Feature set 1 is output by the CNN or a portion thereof. For example, a base block of a CNN including convolutional and pooling layers, which in some embodiments may be a pre-trained network with tuning comprising a plurality of convolutional and pooling layers. In some embodiments, the pre-trained network with tuning also includes one or more fully connected layers and, in one embodiment, an output layer, positioned before the network converges with the patient network at the shared fully connected layers. An output layer (not shown) may be stacked on the last shared fully connected layer to provide an output prediction that includes the processing of both sets of input data through the network. In one embodiment, the output layer stacked on the may include a classification layer as described herein.

With respect to FIG. 11C, the AI model 12 implementation incorporates patient data comprising demographics data by directly feeding the patient data as features to the fully connected layers of the CNN or extension thereof. The AI model provides an example of an AI model 12 that shares a fully connect layer block by receives input from multiple sources. The output of the convolutional and pooling layer block includes activation values corresponding to visual features identified in the input data. These visual features may be output from convoluted or pooling layers.

In various embodiments, the integrated networks of FIG. 11A and/or FIG. 11B may be trained jointly. For example, training may include defining global loss function based on the output of individual networks and tuning all the networks accordingly.

In various embodiments, the system 10 may include an AI model 12 comprising spatial weighting to further improve accuracy. For example, training the network may include identification of areas of interest in input data. Such areas are identified as having the highest probability to allow the AI model 12 to categorize the input data, e.g., images via their activation maps. Using this knowledge, the AI model 12 may be remodeled to look specifically at those areas of interest that have improved accuracy of the algorithm and give those areas more weight. In some embodiments, the AI model 12 may be built off a pre-trained network, e.g., convolutional/pooling layer block, trained with non-medical images and subsequently tuned with medical images such as B-scans, thickness maps, heat maps, structure maps, or bullseye maps. In other embodiments, the AI model 12 may be built off a pre-trained network, e.g., convolutional/pooling layer block, trained with medical images medical images. The AI model 12 may be further tuned with B-scans, thickness maps, heat maps, structure maps, or bullseye maps.

Figure 12:
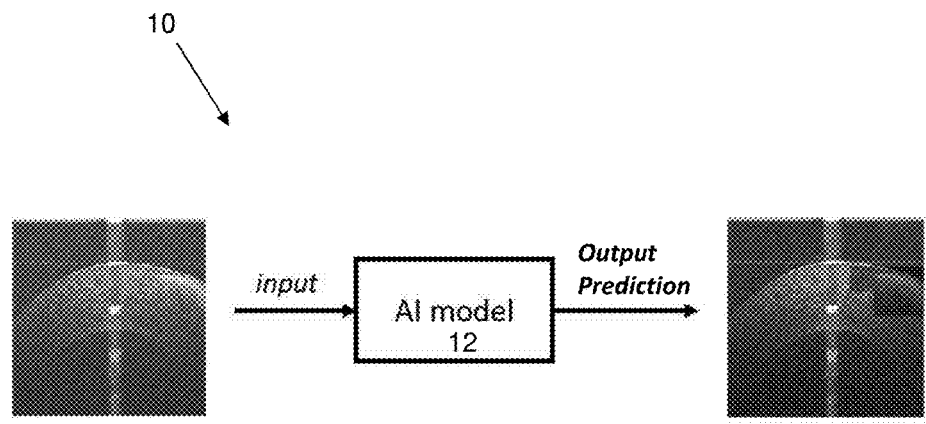
FIG. 12 is a schematic diagram of an embodiment of the system including an AI model for identifying regions important to predictions of certain conditions or diseases of the cornea or anterior segment of the eye according to various embodiments.

FIG. 12 illustrates a further embodiment of the system 10 wherein the AI model 12 includes an AI model to identify important regions of input data. The identification of the important regions in the output may be used to increase the relative weight given to those regions in the algorithm executed by the CNN or other neural network for making diagnosis, risk, treatment, action, or severity predictions with respect to a corneal or anterior segment condition or disease. While shown as being part of system 10, in one embodiment, AI model 12 for identifying important regions of input data may be a separate AI model, which may not be part of system 10. In another embodiment, the AI model for identifying important regions of input data comprises a neural network, which may be an AI submodel of AI model 12 or the same neural network or a version thereof of the neural network for making diagnosis, risk, treatment, action, or severity predictions with respect to a corneal or anterior segment condition or disease. Accordingly, the AI model 12 may include a separate or same model for important region identification. In one example, a same model may be used using an occlusion test. In another example, a different model may be used with respect to modifying the trained network to output an image instead of scores for the conditions.

As illustrated in FIG. 12, a B-scan image is taken as an input and the AI model 12 highlights the regions that are important to predict certain disease in the input image as an output. In some embodiments, the AI model 12 of FIG. 12 may be the same or include one or more of the prediction operations described herein with respect to FIGS. 1A-1J, 4-11, & 13-25. For example, the AI model 12 of FIG. 12 may also be configured to predict one or more of disease, severity, risk, treatment, action, layer segmentation, or combination thereof. The AI model 12 may include integrated or separate submodels, e.g., joint, combined, or stacked. The regions may be detected in the input image from which a prediction is to be generated. This network may have B-scan images or thickness maps as input, for example, with a target to highlight important features in the input image. Therefore, the input in these configurations will typically be an image such as a thickness map or B-scan. However, in one embodiment, an image such as a heat map may be used as input. In some embodiments, B-scans, thickness maps, and/or heat maps may be used. Other patient data may also be used to give prior probability to the image regions. For example, patient data such as demographics or disease or conditions associated with the patient's other eye may be input in to the AI model 12 as described in more detail elsewhere herein and incorporated in to the output, e.g., as weighting.

Figure 13:
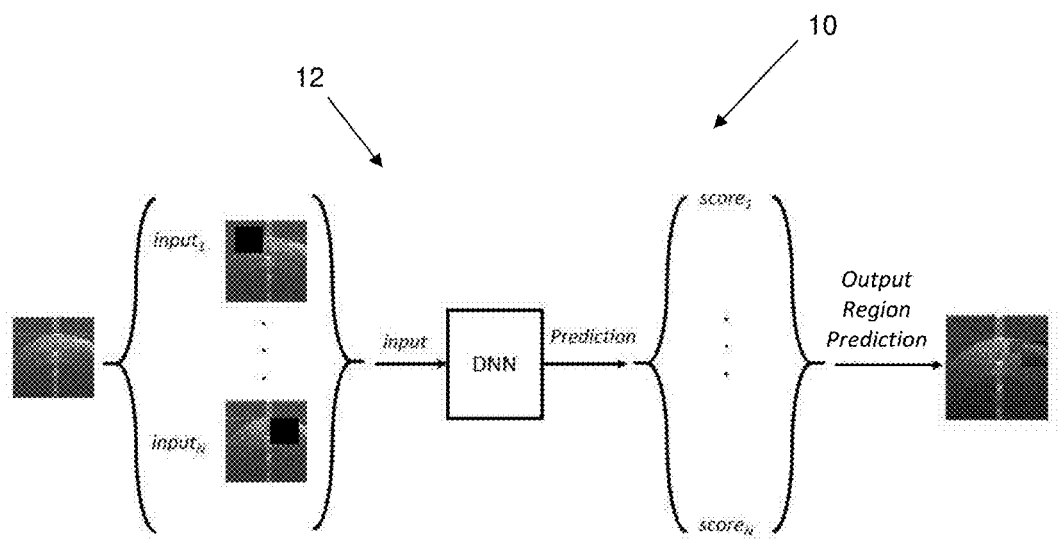
FIG. 13 is a schematic diagram of an implementation of the system according to FIG. 12 performing an occlusion test to identify the important regions in the input image according to various embodiments.

FIG. 13 illustrates an implementation of the system 10 according to FIG. 12. In this embodiment, the AI model 12 includes a DNN and an occlusion test is used to find the important regions in the input image. Multiple copies of an image are input into the AI model with different portions of the image occluded. By comparing the output prediction scores of the various occluded images to an output prediction score obtained from the image without occlusion, important regions may be identified. That is, the occluded parts of the image that account for largest drop in the prediction likelihood may be deemed to be associated with the most important parts in the input image. In some embodiments, the AI model 12 may be configured to output an image that highlights these regions. In the illustrated embodiment, the regions are highlighted in green in the output of the AI model 12. Thus, the AI model 12 used to predict corneal condition or disease probabilities or a similar AI model may be used to predict important regions in the input image where the parts of the image with lower output scores are chosen as the most important, which may be the case when only using the occlusion test. In some embodiments, the system 10 may include the AI model for predicting important regions for incorporation of the identification of important regions into the AI model 12. In the illustrated embodiment, the system 10 outputs the important regions in a report, which may be further incorporated into a health report by an analysis subsystem, but does not receive the important regions as an input. In other embodiments, the system 10 may receive such information as input or for incorporation into the AI model 12. In one embodiment, system 10 includes a preprocessing subsystem that includes the AI model for identification of important regions. In one example, AI model 12 may be implemented to identify important regions during training and such data may thereafter incorporated into the AI model 12 to improve prediction accuracy.

In some embodiments, B-scan images may be preprocessed before identification of important regions. The identification of these regions may be done after the prediction in training data. The predicted regions may be considered part of the generated report and may not be used to enhance a prediction with respect to the image in which the identification relates. However, the predicted regions may be used to further improve prediction to train the networks by guiding the algorithm to look at specific regions to give them more weight.

In another implementation wherein the AI model 12 is configured to identify important regions, the data obtained from the identification of the important regions may be used to modify the last layers of the convolutional/pooling layer portion of a trained network. For example, the modification may comprise grouping the final activation maps of this portion of the network using weights between them and the first fully connected layer. This combination may be used to generate a probability map of the important regions in the images based on the trained network, which may translate to fixed regions for all images and which is different than the occlusion test method.

In addition to improving future predictions by incorporating important region findings in subsequent iterations of the AI model 12. Eye professionals may examine images or eyes a look to specific areas for diagnosis of diseases and conditions of the cornea or anterior segment. The AI model, however, may train the algorithm to look at regions previously unknown to correlate with a disease or condition. Thus, the report generated identifying important regions to the diagnosis provides information regarding how the AI model is operating and provides insight into additional locations where diseases and conditions of the cornea and anterior segment may impact or that may be used to provide a basis for diagnosis or other prediction, such as severity, risk, progression, prognosis, treatments, etc., related to those disease or conditions.

In various embodiments, the AI model 12 may be trained on B-scans. The AI model 12 may then be further trained using one or more thickness maps or heat maps or specific regional images. Additionally or instead, the AI model 12 may take as input one or more maps such as thickness maps, heat maps, structure maps, or bullseye maps.

Figure 14:
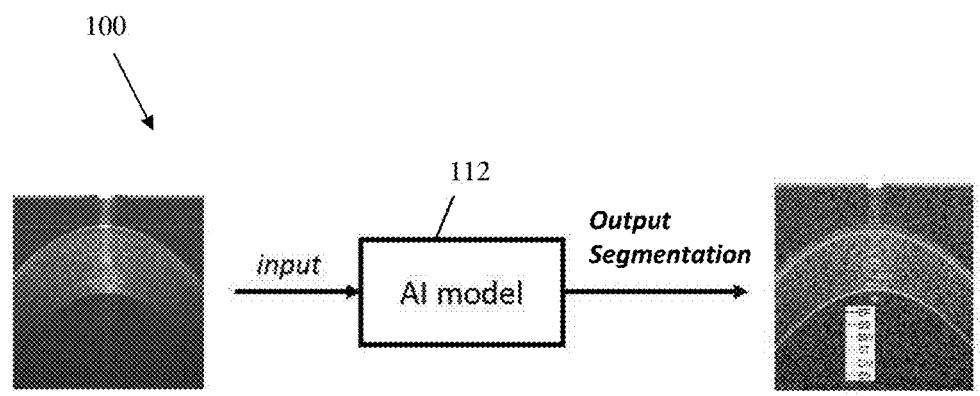
FIG. 14 is a schematic diagram of an embodiment of the system including an AI model for segmenting corneal layer boundaries according to various embodiments.
Figure 15:
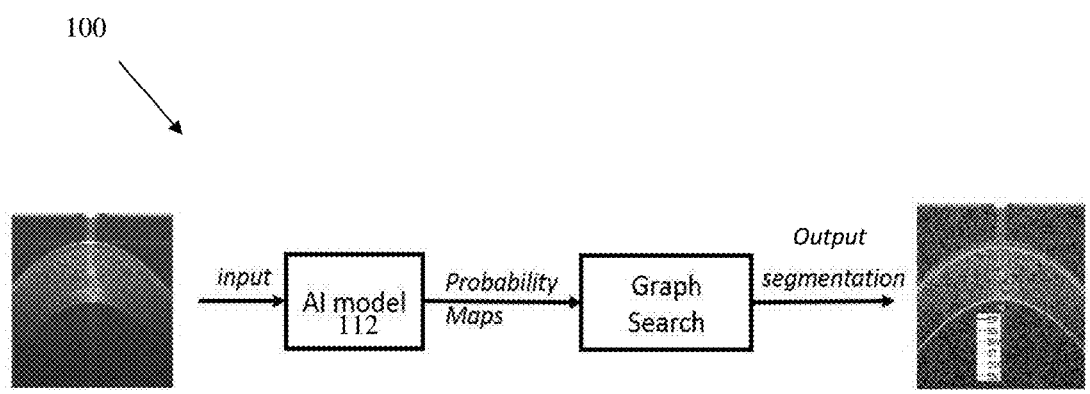
FIG. 15 is a schematic diagram of an embodiment of the system including an AI model for segmenting corneal layer boundaries according to various embodiments.

FIGS. 14 & 15 schematically illustrate a system 100 comprising an AI model 112 trained to output corneal layer segmentation predictions according to various embodiments. In some embodiments, the system 100 may be part of system 10.

The AI model 112 may implement supervised deep learning methods, with labelled input data, be used to improve the corneal layer segmentation task. For example, supervised deep learning methods, with labelled input data, may be used to divide the image into foreground (the cornea) and background. The epithelium and endothelium may be defined as top and bottom boundaries of the cornea. In another implementation, unsupervised deep learning methods may also be used for the segmentation of the anterior segment and epithelium and endothelium, thereby overcoming the problem of labeling the data which requires a lot of time from experts and specialized trained operators. This approach also has the advantage that it can be done using supervised learning with labelled images and used with unsupervised learning by using clustering without any labeling.

In some instances the system 10 may include a preprocessing subsystem (see, e.g., FIG. 1E) including system 100 or AI model 112. In some embodiments, the preprocessing subsystem may further process the image data to denoise the input image or may generate thickness maps, heat maps, structure maps, or bullseye maps. In one example, the preprocessing subsystem produces images of one or more layers from the segmented image data for input into the AI model 12. For example, the preprocessing subsystem may remove one or more segmented layers from the image data. In some embodiments, system 10 may transmit requests to system 100 for segmentation of images. System 100 may then segment one or more images and transmit the segmented image data or data derived therefrom to system 10. Communication may be over a communication network. In one example, system 10 may access system 100 by making an API call over the communication network that includes a segmentation request.

FIG. 14 illustrates a segmentation operation performed by the AI model 112 to segment the corneal layer boundaries. The AI model 112 takes the OCT B-scan as an input and produces the segmentation of the layer boundaries as the output of the AI model 112. The AI model 112 may divide the image into foreground (the cornea) and background. The epithelium (EP, purple) and the endothelium (EN, orange) may be defined as top and bottom boundaries of the cornea. This technique may then be extended to the segmentation to other microlayers of the cornea by sequential identification of subsequent top and boundaries, namely, basal-epithelial (BS, light blue), bowman's (BW, aqua), stroma (ST, green) and descemet's (DM, yellow). For example, the AI model 112 may work from the anterior and/or posterior inward to identify segmentation boundaries. In various embodiments, the AI model 112 comprises a semantic network such as Region-based Convolutional Neural Network (R-CNN), Fully Convolutional Networks (FCN), U-Net, SegNet for the segmentation of the anterior segment and for the segmentation of the epithelium and the endothelium of the cornea. The AI model 112 takes OCT B-scan images as input and generates the segmentation layer boundaries as the output of the model.

FIG. 15 illustrates another embodiment of the system 100 wherein the AI model 112 takes an OCT B-scan as an input and outputs probability maps. The output may include a probability map for each boundary. These maps can be further processed using graph search to find the final segmentation.

Figure 16:
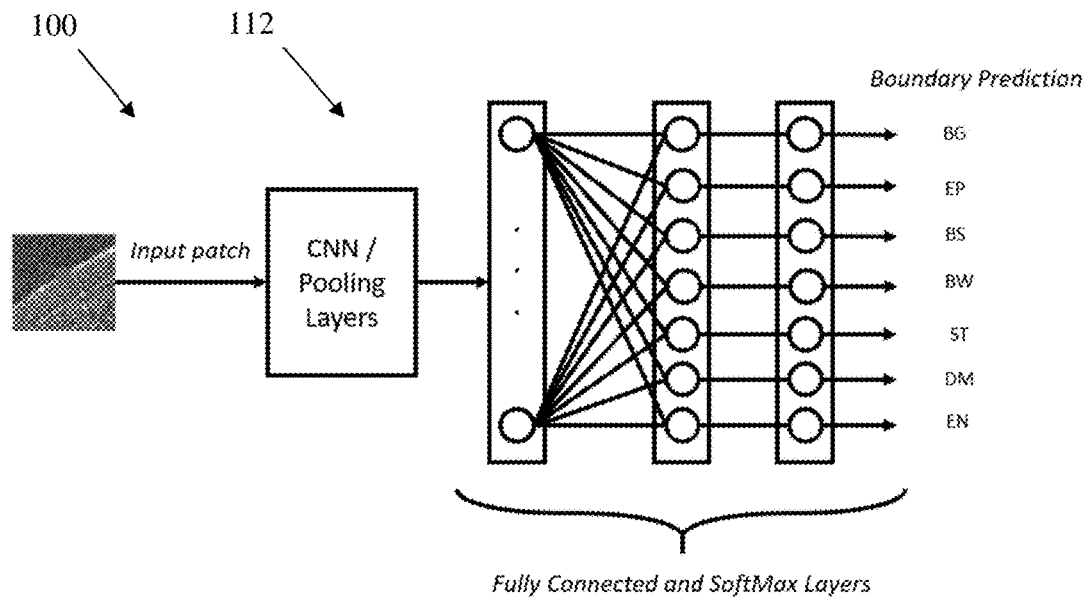
FIG. 16 is a schematic diagram of another embodiment of the system including an AI model for generating boundary predictions for corneal layer segmentation according to various embodiments.

The AI model 112 depicted in FIG. 16 takes as input a small patch of a high definition image, e.g., OCT B-scan, and predicts whether the patch belongs to the background (BG) or one of the boundaries: (EP)—epithelium, (BS)—basal epithelium, (BW)—bowman's layer, (DM)—descemet's membrane, (EN)—endothelium, as shown in the architecture of FIG. 16. In particular, the AI model 12 outputs the probability of the input patch that represents the likelihood of the center of the patch belonging to the background and each of the boundaries. By repeating this for all pixels, a probability map of all pixels belonging to each category may be constructed.

Figure 17:
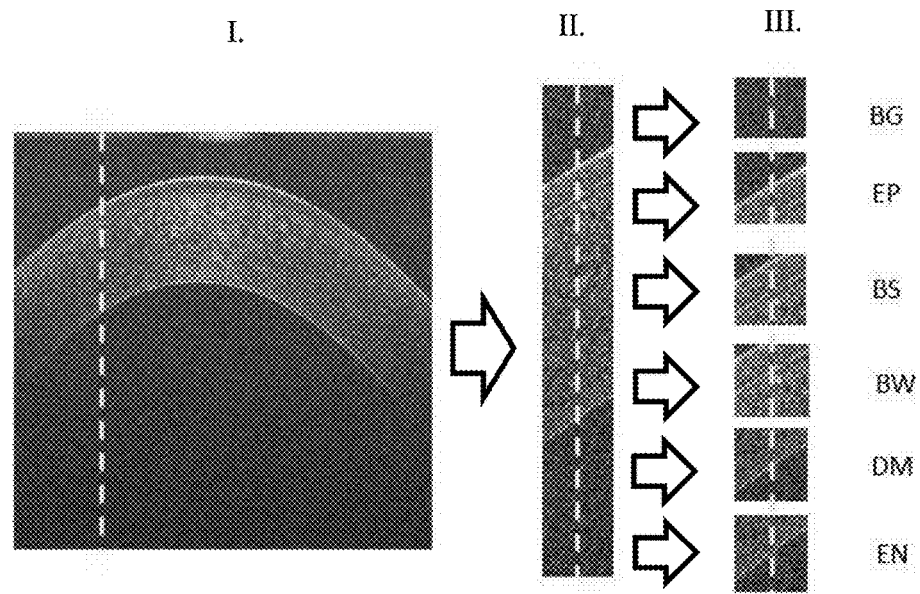
FIG. 17 is a schematic diagram of a patch extraction technique for generating a training dataset and training the AI model of the system described with respect to FIG. 16 according to various embodiments.

FIG. 17 illustrates patch extraction from a B-scan image. The B-scan is shown in panel I. At each A-scan, indicated by the broken vertical line, 7 patches are extracted, one patch belonging to the background (BG) and 6 patches where each one of them belongs to each boundary. As shown in panel II lateral regions flanking the A-scan are also included in the patches shown in panel III. The A-scan is generally centrally positioned in the patch, but in other embodiments the A-scan may be positioned to the left or right of center. This extraction procedure may be repeated for additional A-scans, or all A-scans, making up the B-scan. The extracted patches from the image may be added to extracted patches from the other images to construct a training dataset for the AI model 112.

Testing may be performed similarly where the input image is divided into patches. The patches may be classified by the trained network to give the probability maps of the input image pixels. These probability maps may then be used with graph search to segment the boundaries, e.g., the probabilities of the pixels in the probability maps may be used to identify paths of minimum weight for interface boundaries. Threshold values may be used in one example. Various graph search techniques may be used. In some embodiments, the graph search may be weighted or unweighted.

With further reference to FIGS. 18-23, in various embodiments, the AI model 12 output condition scores that relate to a set of diseases or conditions. The set of conditions scores may further include one or more corresponding scores that additionally relate to ancillary aspect predictions corresponding to the disease or condition such as severity, risk, action/treatment, progression, prognosis, or other predictions corresponding to one or more of the diseases or conditions. In various embodiments, the system 10 may include an AI model 12 comprising a plurality of submodels for each predicted disease or condition configured to predict severity, risk, treatment, progression, prognosis, or other ancillary aspect prediction corresponding to the particular disease or condition. In some embodiments, the AI model 12 may include a combined architecture to perform multiple predictions, such as multiple predictions corresponding to a single disease or condition or multiple predictions corresponding to multiple disease or conditions. For example, a single network may be configured to generate one score including multiple diseases or conditions. This approach may include dividing the data based on all the disease of conditions to have specific data for each augmented category. In one example, a score may correspond to a category comprising a prediction of a disease or condition and one or more ancillary aspects corresponding to the disease or condition, e.g., one or more of severity, risk, action, treatment, progression, prognosis. In another embodiment, a set of condition scores may be generated for multiple diseases or conditions and one or more ancillary aspects selected from severities, risks, actions, treatments, or combinations thereof for one or all of the disease or conditions. In some embodiments, after the system 10 generates a prediction of a disease of condition, the input data upon which the prediction in based may be automatically fed to submodels to generate ancillary aspect predictions corresponding to the disease or condition, such as severity, risk, action, treatment, progression, prognosis, etc. In some embodiments, submodels for ancillary aspect predictions may be specific to a disease or condition, e.g., trained for prediction of risk level for dry eyes, or may be generic to one or more diseases or conditions.

Figure 18:
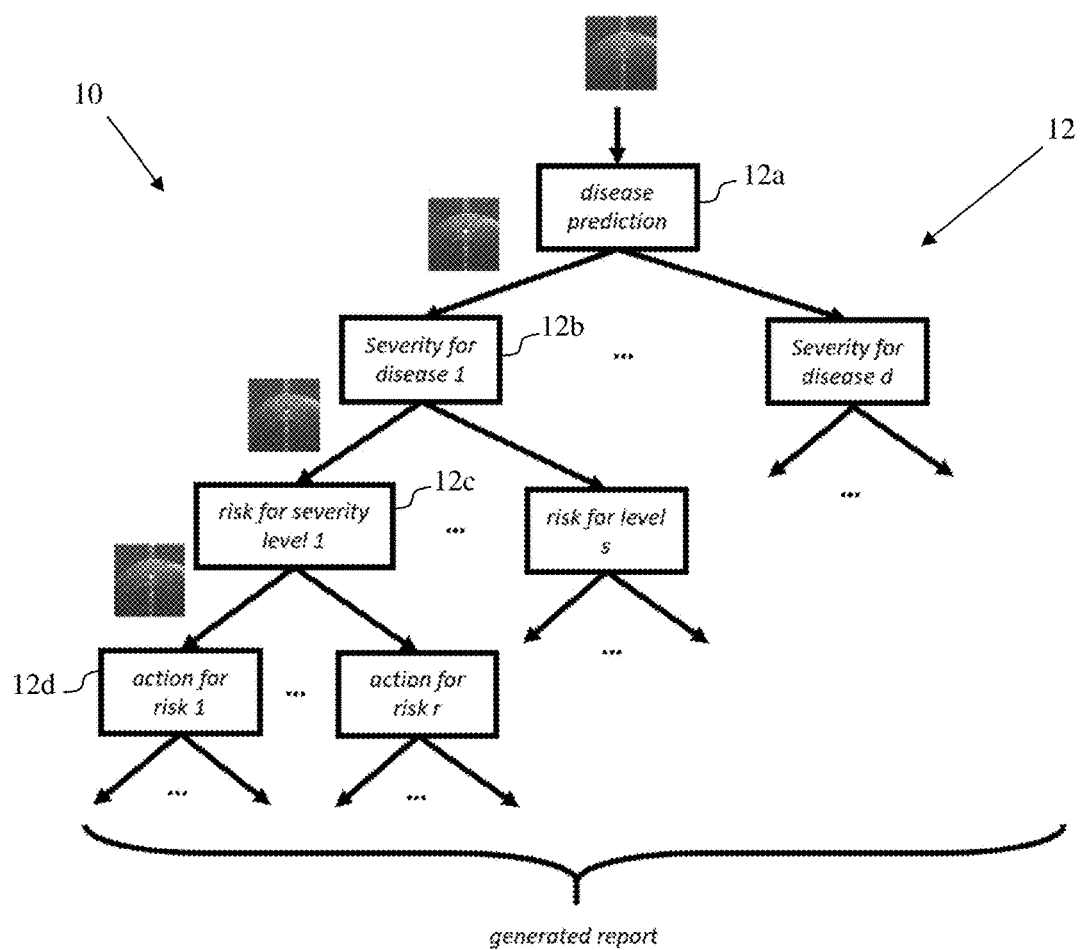
FIG. 18 is a schematic diagram of an embodiment of the system including a hierarchical, cascading architecture according to various embodiments.

FIG. 18 schematically illustrates an embodiment of the system 10 in which the AI model 12 includes a plurality of submodels arranged in a hierarchical design having a cascade configuration. The system 10 may generate a health report using individual networks/submodels. In some embodiments, the generated report may be assembled by an analysis subsystem, as described above. The input data, B-scan in this example, is input into a first tier submodel 12a for generating a disease or condition prediction. The disease or condition prediction, e.g., highest or threshold probability, determines which condition related submodel the input data is to be processed for the next ancillary aspect prediction related to the disease or condition in the following tier. Thus, in this AI model 12, the disease or condition and ancillary aspect predictions in preceding tiers are related. In this example, submodel 12a predicts disease 1. Accordingly, the input data is fed into second tier submodel 12b which is trained to output severity predictions for disease 1. Prediction of another disease category results in the input data being fed into the corresponding second tier submodel for that disease, these submodels are identified by disease d.

In this embodiment, submodel 12b outputs severity levels, but in other embodiments, severity may be output as a score instead of a discrete value. The severity level predicted from submodel 12b determines the third tier submodel that the input data will be fed. As shown, submodel 12b outputs severity level 1 and the input data is provided as input into submodel 12c, which is trained to output risk predictions for disease 1 and severity level 1. Prediction of another severity level results in the input data being fed into the corresponding third tier submodel for that severity level, these submodels are identified by risk for level s.

Submodel 12c outputs risk 1, which results in the input data being provided to submodel 12d trained to output action predictions for disease 1, severity level 1, and risk 1. Prediction of another risk results in the input data being fed into the corresponding fourth tier submodel for that risk, these submodels are identified by action for risk r. The output prediction of submodel 12d may similarly determine subsequent submodels for subsequent ancillary aspect predictions, such as progression or prognosis with or without undertaking the predicted action from submodel 12d. The predictions from each submodel 12a-12d may be provided in a report.

It should be noted, that in some embodiments, one or more of the submodels for ancillary aspect predictions related to the disease or condition may be generic for the disease or condition or for other ancillary aspect conditions. For example, a risk may be generic for two or more severity ranges or levels. In another embodiment, the disease prediction from submodel 12a results in the input data being input into each submodel of a set of condition related submodels for the disease or condition predicted, the selection of which does not relate to the prediction of a subsequent condition related submodel. The set of condition related submodels may include a model for each ancillary aspect prediction to be made, e.g., severity, risk, treatment, action, progression, prognosis, etc. As noted above, multiple diseases or conditions may be predicted, e.g., have associated probabilities above a threshold. In some such embodiments, the input data may be input into a different set of condition related submodels as well. In further embodiments, the input data may be input along a condition related submodel cascade for additional diseases or conditions, e.g., when output probabilities for multiple diseases or conditions are above threshold probabilities for each of the diseases of conditions.

FIG. 19A schematically illustrates an embodiment of the system 10 wherein the AI model 12 is augmented to generate an augmented category. The AI model 12 may be trained to output scores corresponding to an augmented category that includes a single score corresponding to a disease or condition and one or more ancillary aspect predictions corresponding to the disease. The system 10 may generate health report using one network to generate an augmented category including all the values needed for the report. In some embodiments, the generated report may be assembled by an analysis subsystem, as described above. The AI model 12 may be trained using training data comprising grouped images that labeled and annotated for a disease or condition and one or more ancillary aspect predictions. The AI model 12 may use all the annotations at the same time for category prediction. For example, the table in FIG. 19B illustrates that a category ($c_k$) may be based on 5 annotations ($d_k$, $s_k$, $r_k$, $a_k$, $t_k$) wherein the presence of the 5 annotations corresponds to a label of the corresponding category ($c_k$) being used. Thus, a label or category may be included for each combination of disease, severity, risk, action, and treatment. In some embodiments, different, fewer, or more annotations may be grouped in categories. Further to the above, the AI model 12 includes an augmented model to generate an analysis report, which may be a health report. The augmented model is designed as one model that can do all classification tasks at one time. However, in some embodiments, multiple combinations of augmented submodels may be used that perform subsets of classification tasks, e.g., combinations of disease, severity, risk, action, or treatment. The augmented model may be constructed by dividing training data at a detailed level. For example, training data related to specific disease, specific risk, specific treatment, specific action, and specific treatment may be grouped together and these labels will be encoded into a unique augmented label that represent this combination of the original labels. The augmented label will be used in the training. In this way, multiple models may be combined into one model. Such an augmented model takes as input the data divided at very fine levels along with augmented labels. FIG. 19C illustrates an example implementation of the system 10 in FIG. 19A wherein the AI model 12 includes a convolutional/pooling layer block, fully connected layers, and a SoftMax layer.

Figure 20:
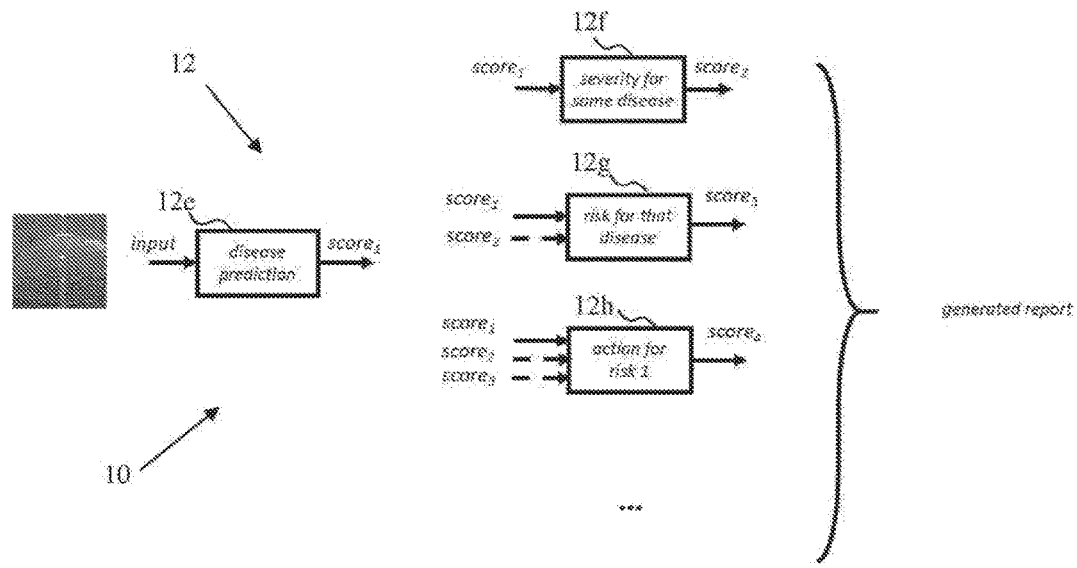
FIG. 20 is a schematic diagram of an embodiment of the system including an AI model having hierarchical architecture utilizing prediction scores according to various embodiments.

FIG. 20 schematically illustrates an embodiment of the system 10 wherein the AI model 12 is configured to output a disease or condition prediction and one or more ancillary aspect predictions related to the disease or condition. In this embodiment, the AI model 12 includes a plurality of submodels 12e-12h. The output score of the first submodel 12e may be used to determine ancillary aspect predictions related to that output. For example, submodel 12e outputs a $score_1$. Thus, in some embodiments, the AI model 12 may include a cascade aspect similar to that described with respect to FIG. 18. That $score_1$ may indicate a disease or may be used by a submodel trained to take that output $score_1$ and determine an ancillary aspect prediction, which may be a score that may or may not ultimately be converted to a category label. As shown, $score_1$ is used as input into submodel 12f which outputs a $score_2$ corresponding to a severity for a disease or condition. In some embodiments, submodel 12f is generic for one or more diseases and the severity score of submodel 12f indicates a disease prediction from which it corresponds. In another embodiment, submodel 12f is specific to a disease or condition and is only triggered to fire if $score_1$ is suitable, e.g., positive, or calculates a suitable $score_2$. $Score_1$ is also input into submodel 12g to generate a $score_3$ corresponding to a risk for the disease or condition corresponding to the severity generated by submodel 12f. As indicated by the broken arrow, submodel 12f may, in some embodiments, optionally take as input $score_2$. $Score_1$ is also input into submodel 12h to generate a $score_4$ corresponding to an action for the risk $score_3$ generated by submodel 12g. As indicated by the broken arrows, submodel 12h may, in some embodiments, optionally take as input $score_2$ and/or input $score_3$.

It will be appreciated that the order of ancillary aspect prediction submodels and the particular input score combinations may be arranged differently for some conditions or diseases within the AI model 12 or other AI models configured to provide other ancillary aspect predictions.

The scores may be obtained from a SoftMax layer before the scored are converted into category labels. That is, model outputs include scores or probabilities which can be converted into the label corresponding to the category with the maximum value by the SoftMax layer. The label may be generated for the report, for example. In some embodiments, one or more of submodels 12f, 12g, or 12h comprises a classical classifier. For example, the score or probability output from one or more submodels 12e-12h may be used as input into a classical classifier, such as the SVM, to train it to detect the scores for the ancillary aspect predictions. In some embodiments, the generated report may be assembled by an analysis subsystem, as described above.

Figure 21:
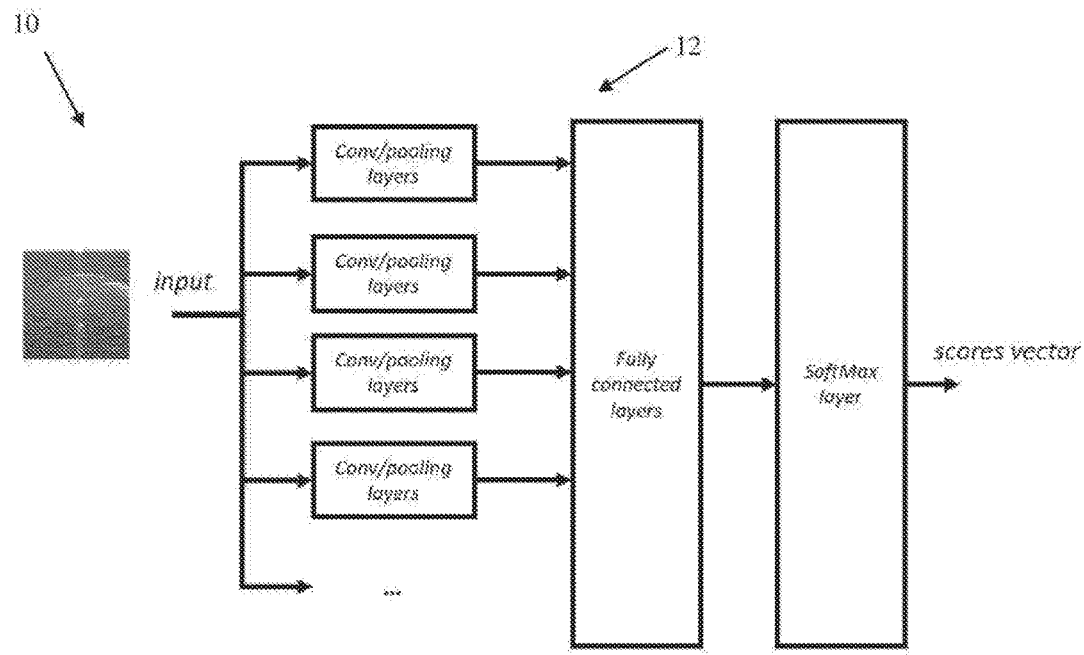
FIG. 21 is a schematic diagram of an embodiment of the system including an AI model having multiple specialized convolutional/pooling layer blocks that connect to a same block of fully connected layers according to various embodiments.

FIG. 21 schematically illustrates an embodiment of the system 10 wherein the AI model 12 includes a Joint network that detects all scores at once. The AI model 12 is an example of converging network. In contrast to the augmented network described with respect to FIGS. 19A-19C that includes a single convolutional/pooling layers block, this AI model 12 includes convolutional/pooling layer blocks. Each may be trained for a particular disease or condition to allow different features to be extracted for each condition. The last layers of each convolutional/pooling layer blocks regroup the extracted features into one set of fully connected layers and SoftMax layer. In some embodiments, the generated report may be assembled by an analysis subsystem, as described above.

Figure 22:
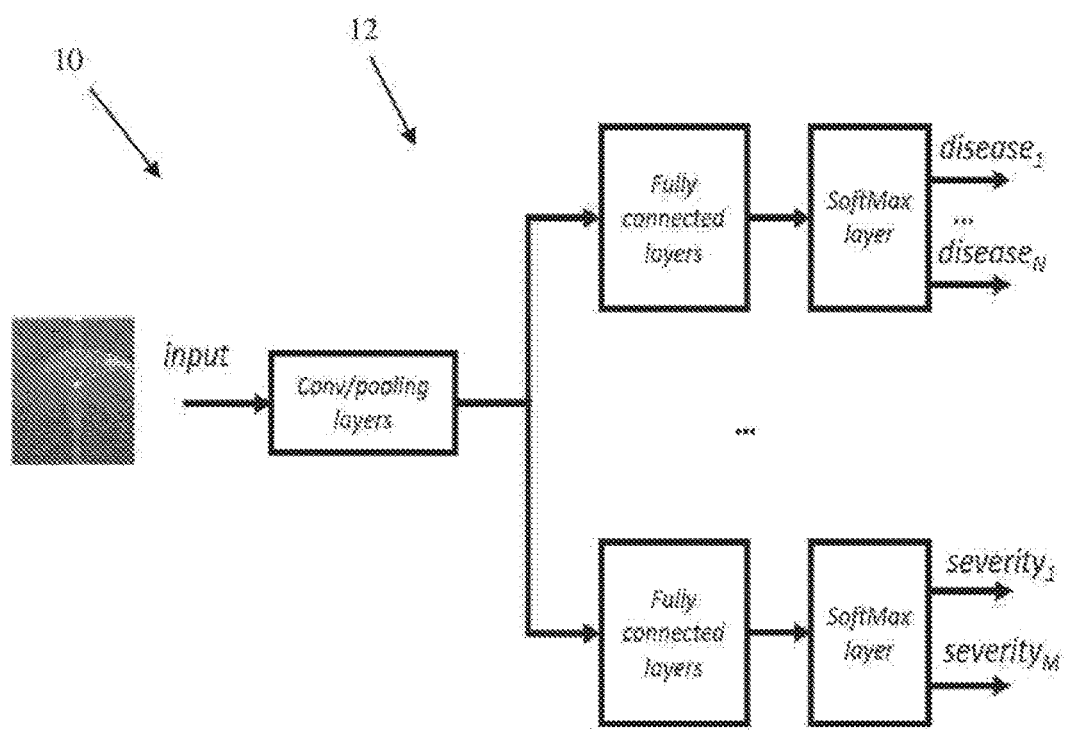
FIG. 22 is a schematic diagram of an embodiment of the system including an AI model having a shared convolutional/pooling layer block that feeds multiple specialized fully connected layer blocks according to various embodiments.

FIG. 22 schematically illustrates an embodiment of the system 10 wherein the AI model 12 includes a combined or combination network using one con/pooling layers block and multiple sets of fully connected layers and SoftMax layers. The AI model is an example of a diverging network. In this case, extracted features will be the same for all conditions. The different predictions share the same set of convolutional and pooling layers but each has its own fully connected layers and SoftMax layer. As shown, a set of fully connected layers and SoftMax layer may be trained to provide a prediction with respect to a set of diseases or conditions. The sets of fully connected layers and SoftMax layer for ancillary aspect predictions may be specific to particular diseases or conditions or may be configured to output a type of ancillary aspect prediction for multiple conditions. In some embodiments, the generated report may be assembled by an analysis subsystem, as described above.

An example training process set up according to various embodiments may include obtaining labeled data or annotating data to obtain labeled data. The labeled data may include training data such as annotated/labeled images. The method may include dividing the labeled data into subgroups where each has the same label that will be predicted by the network. Each data member of the group will have the same label (or set of annotations) and each label group represents a prediction category that will be predicted by the network. The number of data examples in each group is preferably similar so that the data is balanced to prevent bias in the training process toward a specific label. The training data set may include multiple frames for B-scans. Optionally, all frames for each B-scan can be used. Although the frames represent the same cut, they have different noise pattern and slightly different deformation of the cut. Thus, training with multiple frames may be used to make the network robust to noise. The number of layers and their parameters may be determined on basis of experiments and cross validation of the training data. Cross validation is done by dividing the training data into a training part and a validation part. The trained network is then used to test the validation part. This process may be repeated by dividing the training data into another different training set and another different validation set which is evaluated with the new trained network. Therefore, the whole training process may be repeated many times with different subsets of the training data and the trained network may be evaluated with different validation subsets. This may be done to ensure the robustness of the trained network. The trained network may then be evaluated using the real testing data.

Parameters of the model layers may be determined based on various criteria, e.g., input data or image size and/or results of the training experiments. The number of layers may be determined based on data size, e.g., number of images, results of the training experiments, and/or other criteria.

In various embodiments, cross-validation employs exhaustive or non-exhaustive cross-validation such as holdout, K-fold, or Monte Carlo cross-validation.

EXAMPLES

Figure 23:
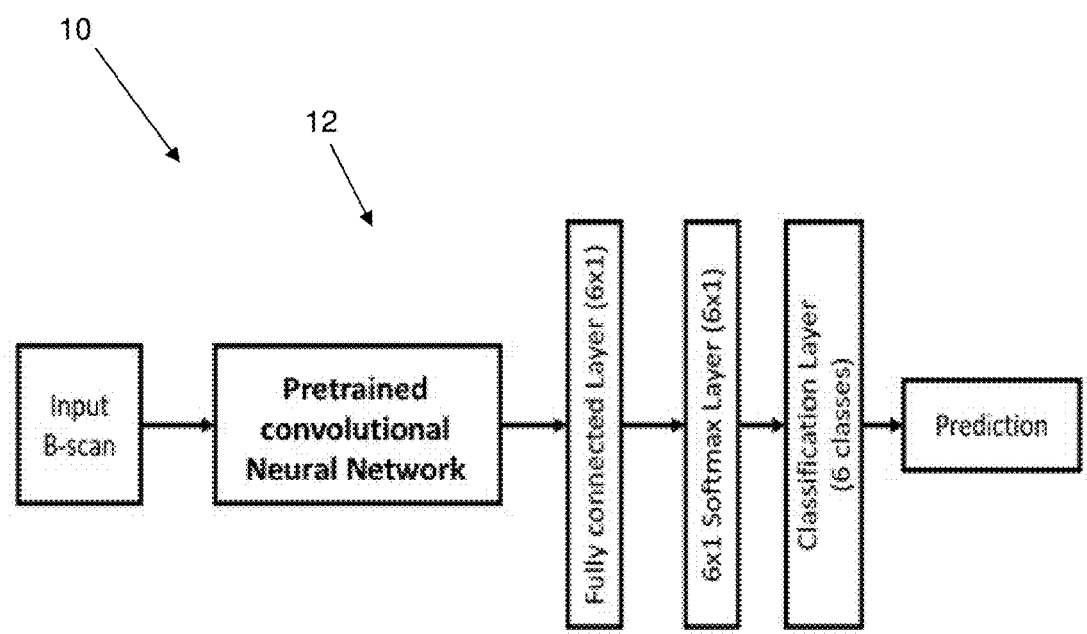
FIG. 23 is a schematic diagram of an embodiment of the system including an AI model incorporating transfer learning according to various embodiments.

A system designed for predicting a corneal or anterior segment condition or diagnosis as described herein. A schematic depiction of the system 10 is shown in FIG. 23.

The system 10 includes an AI model 12 comprising a CNN. In particular, the AI model 12 includes a set of convolutional and pooling layers followed by a set of fully connected layers and an output layer. In this embodiment a modified pre-trained network was incorporated into the AI model 12 architecture of the system 10. The initial layers of a convolutional neural network, e.g., convolutional and pooling layers, are important for feature extraction. The extracted features are generic and may be considered data independent. The last layers, e.g., fully connected layers, combine the important features for each class in the data and are typically dependent on the images used. For the AI model 12, these layers were redefined from that of the pre-trained network. In particular, the fully connected layer and output layer were redefined. In this configuration, the output layer used included a SoftMax layer and a classification layer. These layers are modified to be adapted to the new classification task as follows: the fully connected layer is modified to be of a length equal to the number of categories in the prediction task; the SoftMax layer is modified accordingly to convert the output of the fully connected layer into prediction probabilities; and the classification layer was modified to have the labels corresponding to the new classification problem. For example, for the disease prediction task, the length nodes in the fully connected layer were changed to 6 and the labels were changed to{"Control", "Dry eye", "Fuchs Endothelial Dystrophy", "Keratoconus", "Corneal Graft Rejection", "Limbal Stem Cells Deficiency" }. Each label corresponds to a corneal diagnosis.

Microlayer tomography CML-T B-scan data were used to train the parameters of the fully connected layer and tune the parameters of the original network such that the prediction of the network was optimized for the task of corneal diagnosis. For the task of classifying the severity of corneal the diseases the AI model was trained on OCT CML-T images of different disease severity as graded by the cornea specialist.

During the training stage, all available CML-T frames were used without registration or averaging. This helped the AI model 12 become robust to noise because noise is random while corneal microlayers patterns and features are not. The distinct artifacts associated with anterior segment OCT images may or may not exist in another OCT image e.g. specular reflections, and horizontal artifacts. In further embodiments, the accuracy of the AI model may be further improved by using preprocessed OCT images, and removing those artifacts beforehand (see. e.g., FIGS. 3A & 3B and accompanying discussion). In some embodiments, training the AI model 12 comprises training with B-scan images with averaging and/or registration.

To further improve accuracy, after the 1st training session of the AI model 12, areas of interest on the CML-T OCT images were identified (see, e.g., FIGS. 12 & 13 and accompanying discussion). These areas were found to have the highest probability to allow the neural network to categorize the images (activation maps). Using this knowledge, the AI model was further remodeled to look specifically at those areas of interest and give those areas more weight.

In this demonstration, transfer learning with pre-trained networks was used to reduce training time. However, in other embodiments, the feature extraction layers, such as convolutional layers, of the AI model may be trained on medical images. Although, the training data of the network is not medical images, these data help the network to learn how to extract complex visual features from the image. Convolutional neural networks (such as AlexNet, VGG16, VGG19, and GoogLeNet) may be modified for the classification of corneal diseases using OCT corneal microlayer tomography B-scans (CML-T), thickness maps, and heat maps of the cornea. Here, the last three layers in each network were modified to be suitable for the classification task and then tuned their parameters using approximately 14,000 corneal B-scan CML-T images. These CML-T B-scans represented different corneal diseases and where used as a dataset to train and tune the neural network of the deep learning algorithm. The diagnosis of each of the CML-T B-scan was made by a cornea specialist. Eighty percent of this dataset was utilized for training and 20% was utilized for testing and evaluation of the network.

In this demonstration, the AI model was allowed to provide up to two diagnoses for the same eye (if a second diagnosis was present). The probability of diagnosis was calculated by the network, and if a second diagnosis was calculated to have a probability above a threshold, then that second diagnosis was also provided. For example, the diagnosis could be Keratoconus with Dry eye. The accuracy of the model was further improved by calculating the probability of the diagnosis for each single CML-T OCT B-scan and then getting a mean of probability from the total B-scans of the same eye. The results of the demonstration are summarized in Table. 1. As can be seen in Table 1, the AI model to classify corneal CML-T B-scans achieved accuracy of 98.85% for the classification task.

TABLE 1

| Label | Training accuracy (%) | Testing accuracy (%) |
| --- | --- | --- |
| control | 97.44 | 96.72 |
| dry | 98.18 | 96.88 |
| fuchs | 99.96 | 99.85 |
| graft_rejection | 99.00 | 98.80 |
| kcn | 98.61 | 96.91 |
| stem_cells | 99.87 | 100.00 |
| Overall accuracy | 98.77 | 98.18 |

As can be seen, the system 10 include a technique to use artificial intelligence in OCT corneal microlayer tomography to assist in the diagnosis of corneal diseases. DL methods are used to automate the tasks needed for diagnosis. As shown in FIG. 23 and the accompanying discussion the system 10 may utilize transfer learning and incorporate pre-trained networks to reduce the training time. As noted above, on top of the pre-trained network, the system 10 may include additional layers for a desired classification task. For example, the system 10 may include a convolutional neural network architecture. The system 10 may then tune parameters using, e.g., thickness maps, heat maps, OCT B-scans, or color images.

The AI model 12 may similarly, be trained for additional prediction tasks such as severity, risk, progression, treatment, response to treatment, or other predictions. The AI model 12 may include a combined or augmented model and/or one or more submodels that may be separately or jointly trained as described above and elsewhere herein to generate other or ancillary aspect predictions. Notably, the processes, operations, and methods described herein with respect to the system 10, 100 may further incorporate any of the features and functionality described for the system 10 or as otherwise described herein. In various embodiments, the system 10, 100 is a system that can be implemented as computer application, web application or a smartphone application that implements some of or all the techniques described herein.

Figure 24:
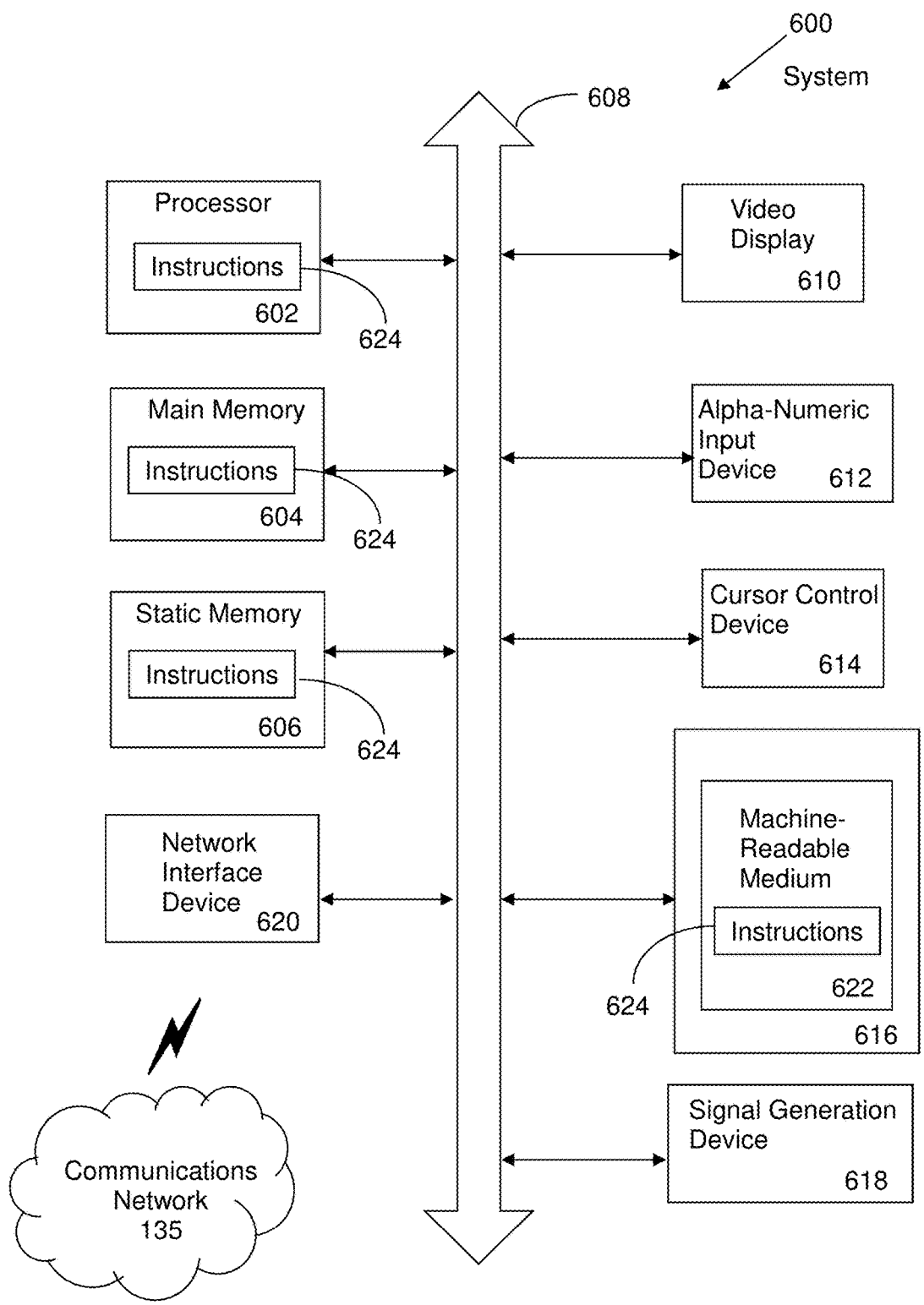
FIG. 24 is a schematic diagram of a machine in the form of a computer system within which a set of instructions, when executed, may cause the machine to perform any one or more of the methodologies or operations of the systems and methods for analyzing and processing input data associated with the cornea or anterior segment of the eye through the use of machine learning to generate predictions.

Referring now also to FIG. 24, at least a portion of the methodologies and techniques described with respect to the exemplary embodiments of the system 10, 100 may incorporate a machine, such as, but not limited to, computer system 600, or other computing device within which a set of instructions, when executed, may cause the machine to perform any one or more of the methodologies or functions discussed above. The machine may be configured to facilitate various operations conducted by the system 10, 100. For example, the machine may be configured to, but is not limited to, assist the system 10, 100 by providing processing power to assist with processing loads experienced in the system 10, 100 by providing storage capacity for storing instructions or data traversing the system 10, 100 or by assisting with any other operations conducted by or within the system 10, 100.

In some embodiments, the machine may operate as a standalone device. In some embodiments, the machine may be connected (e.g., using communications network 135, another network, or a combination thereof) to and assist with operations performed by other machines, programs, functions, and systems, such as, but not limited to, the system 10, 100 AI model, database, analysis subsystem, OCT imaging system, OCT image library, preprocessing subsystem, map generator, computing and communication devices, patient network, pre-trained network, CNN, any device, system, and/or program in FIGS. 1A-23, or any combination thereof. The machine may be connected with any component in the system 10, 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein. In one example, AI model may be executed using one or more servers.

The computer system 600 may include a processor 602 (e.g., a central processing unit (CPU), a graphics processing unit (GPU, or both), a main memory 604 and a static memory 606, which communicate with each other via a bus 608. The computer system 600 may further include a video display unit 610, which may be, but is not limited to, a liquid crystal display (LCD), a flat panel, a solid state display, or a cathode ray tube (CRT). The computer system 600 may include an input device 612, such as, but not limited to, a keyboard, a cursor control device 614, such as, but not limited to, a mouse, a disk drive unit 616, a signal generation device 618, such as, but not limited to, a speaker or remote control, and a network interface device 620.

The disk drive unit 616 may include a machine-readable medium 622 on which is stored one or more sets of instructions 624, such as, but not limited to, software embodying any one or more of the methodologies or functions described herein, including those methods illustrated above. The instructions 624 may also reside, completely or at least partially, within the main memory 604, the static memory 606, or within the processor 602, or a combination thereof, during execution thereof by the computer system 600. The main memory 604 and the processor 602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 622 containing instructions 624 so that a device connected to the communications network 135, another network, or a combination thereof, can send or receive voice, video or data, and communicate over the communications network 135, another network, or a combination thereof, using the instructions. The instructions 624 may further be transmitted or received over the communications network 135, another network, or a combination thereof, via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Unless specifically stated otherwise, discussions herein using words such as "processing," "generating," "detecting," "analyzing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

It will be appreciated by those skilled in the art upon reading the present disclosure that the system 10 described herein (e.g., see FIG. 1A) may include an AI model 12 comprising multiple AI networks or models, e.g., submodels, as described above and elsewhere herein. For example, the AI model 12 may include a submodel for generating a disease prediction and one or more submodels for generating ancillary aspect predictions corresponding to the disease prediction (e.g., severity, risk, progression, action or treatment, or treatment response). In some examples, the submodels for generating ancillary aspect predictions may be generic or specific to a disease prediction. In one example, the submodels for generating ancillary aspect predictions may be specific to a disease and one or more other ancillary aspect predictions or categories thereof. In another example, the submodels for generating ancillary aspect predictions may take as input the same or different input. In some embodiments, the submodels for generating ancillary aspect predictions take as input one or more scores generated by other submodels. In various embodiments, the AI model 12 may comprise any network architecture described herein, e.g., as described herein with respect to FIGS. 1A-1J, FIGS. 4-16, or FIGS. 18-23. In various embodiments, the AI model 12 described with respect to FIGS. 1A-1J, FIG. 4, or FIG. 5 includes multiple submodels including two or more of the AI models 12 described with respect to FIGS. 6-16. In some such embodiments, the AI model 12 may include multiple submodels of one or more of the AI models 12 described with respect to FIGS. 6-16. In various embodiments, any of the above AI models 12 may include (e.g., integrate or operatively combine with, which may include an analysis subsystem including important region predictions in a health report) the AI subsystem 12 described with respect to FIGS. 12-13. Similarly, any of the above AI models 12 may incorporate patient data, such as demographic data, as described with respect to FIG. 11A-11C. Any of the above embodiments, may also take as input any input data described herein, including FIGS. 2A-3B.

The illustrations of arrangements, including embodiments, examples, and implementations, described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims. The conjunction or is intended to be inclusive unless indicated otherwise and may be used interchangeably with the conjunction and/or.

As used herein any reference to "one embodiment" "some embodiments" "various embodiments" "an embodiment" "example" "instance" "configuration" or the like means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A system for facilitating neural-network-based determinations of corneal conditions, the system comprising:
   a neural network comprising a plurality of layers, the plurality of layers comprising:

at least one input layer configured to take, as associated inputs, both an image of one eye and an image of another eye; and at least one hidden layer configured to (i) obtain a first prediction related to presence of a corneal condition in the one eye, (ii) obtain a second prediction related to presence of the corneal condition in the other eye, and (iii) adjust at least one of the first or second predictions based on the other one of the first or second predictions; and one or more processors executing computer program instructions that, when executed, cause the one or more processors to:

for each eye of at least one subject, provide multiple frames of a same image cut from a corneal scan of the eye to the neural network to train the neural network, the neural network generating at least one prediction related to presence of at least one corneal condition for the eyes of the at least one subject based on the multiple frames of the same image cut;

subsequent to the training of the neural network, provide, as associated inputs, an image of a first eye of a subject and an image of a second eye of the subject to the neural network; and obtain, via the neural network, one or more predictions related to presence of at least one corneal condition for the first and second eyes of the subject, the neural network generating the one or more predictions based on the images of the first and second eyes.

2. The system of claim 1, wherein the at least one hidden layer is configured to perform the adjustment by applying a weight associated with the first prediction to the second prediction to adjust the second prediction.

3. The system of claim 1, wherein the at least one hidden layer is configured to perform the adjustment by adjusting the second prediction based on the first prediction indicating that the corneal condition is present in the one eye.

4. The system of claim 1, wherein the at least one input layer is configured to take, as associated inputs, the images of the one eye and the other eye and one or more thickness maps, and wherein the neural network is configured to generate the first and second predictions based on the images of the one eye and the other eye and the one or more thickness maps.

5. The system of claim 1, wherein providing the multiple frames comprises providing multiple raw frames of the same image cut from the corneal scan to the neural network such that each frame of the multiple raw frames of the same image cut comprises different noise patterns from other frames of the multiple raw frames.

6. The system of claim 1, wherein the one or more processors are caused to:

provide multiple raw frames of a first image cut of the first eye and multiple raw frames of a second image cut of the second eye to the neural network to obtain the one or more predictions, wherein the neural network generates the one or more predictions based on the multiple raw frames of the first and second image cuts.

7. The system of claim 1, wherein the one or more predictions relate to presence of at least one of corneal ectasia, Keratoconus, corneal graft rejection episode and failure, dry eye syndrome (DES), Fuchs' dystrophy, corneal limbal stem cell deficiency, cataract, or glaucoma.

8. The system of claim 1, wherein the one or more predictions relate to presence of two or more of corneal ectasia, Keratoconus, corneal graft rejection episode and failure, dry eye syndrome (DES), Fuchs' dystrophy, corneal limbal stem cell deficiency, cataract, or glaucoma.

9. A method implemented by one or more processors executing computer program instructions that, when executed, perform the method, the method comprising:

providing a prediction model comprising a plurality of layers, the plurality of layers comprising:

at least one input layer configured to take, as associated inputs, corneal images associated with one another;

at least one output layer configured to output one or more cornea-related predictions; and at least one hidden layer between the at least one input layer and the at least one output layer, the at least one hidden layer being configured to (i) obtain a first prediction related to presence of a corneal condition, (ii) obtain a second prediction related to presence of the corneal condition, and (iii) adjust at least one of the first or second predictions based on the other one of the first or second predictions, wherein the first prediction is derived from one of the associated corneal images, and the second prediction is derived from another one of the associated corneal images;

providing, as associated inputs, a first corneal image associated with a subject and a second corneal image associated with the subject to the prediction model; and obtaining, via the prediction model, one or more predictions related to presence of at least one corneal condition for the subject, the prediction model generating the one or more predictions based on the first and second corneal images.

10. The method of claim 9, wherein the at least one hidden layer is configured to perform the adjustment by applying a weight associated with the first prediction to the second prediction to adjust the second prediction.

11. The method of claim 9, wherein the at least one hidden layer is configured to perform the adjustment by adjusting the second prediction based on the first prediction indicating that the corneal condition is present in an eye of the subject.

12. The method of claim 9, wherein the at least one input layer is configured to take, as associated inputs, the corneal images and one or more thickness maps, and wherein the prediction model is configured to generate the first and second predictions based on the corneal images and the one or more thickness maps.

13. The method of claim 9, further comprising:

providing multiple frames of a same image cut from a corneal scan to the prediction model to train the prediction model, the prediction model generating at least one prediction related to presence of at least one corneal condition based on the multiple frames of the same image cut.

14. The method of claim 13, wherein providing the multiple frames comprises providing multiple raw frames of the same image cut from the corneal scan to the prediction model such that each frame of the multiple raw frames of the same image cut comprises different noise patterns from other frames of the multiple raw frames.

15. The method of claim 9, further comprising:

providing multiple raw frames of a first image cut from a first corneal scan and multiple raw frames of a second image cut from a second corneal scan to the prediction model to obtain the one or more predictions, wherein the prediction model generates the one or more predictions based on the multiple raw frames of the first and second image cuts.

16. The method of claim 9, wherein the one or more predictions relate to presence of at least one of corneal ectasia, Keratoconus, corneal graft rejection episode and failure, dry eye syndrome (DES), Fuchs' dystrophy, corneal limbal stem cell deficiency, cataract, or glaucoma.

17. The method of claim 9, wherein the one or more predictions relate to presence of two or more of corneal ectasia, Keratoconus, corneal graft rejection episode and failure, dry eye syndrome (DES), Fuchs' dystrophy, corneal limbal stem cell deficiency, cataract, or glaucoma.

18. The method of claim 9, wherein the prediction model comprises a neural network.

19. One or more non-transitory computer-readable media comprising computer program instructions that, when executed by one or more processors, cause operations comprising:
providing a prediction model comprising a plurality of layers, the plurality of layers comprising:
at least one input layer configured to take, as associated inputs, corneal images associated with one another;
at least one output layer configured to output one or more cornea-related predictions; and
at least one hidden layer between the at least one input layer and the at least one output layer, the at least one hidden layer being configured to (i) obtain a first prediction related to presence of a corneal condition, (ii) obtain a second prediction related to presence of the corneal condition, and (iii) adjust at least one of the first or second predictions based on the other one of the first or second predictions, wherein the first prediction is derived from one of the associated corneal images, and the second prediction is derived from another one of the associated corneal images;
providing, as associated inputs, a first corneal image associated with a subject and a second corneal image associated with the subject to the prediction model; and
obtaining, via the prediction model, one or more predictions related to presence of at least one corneal condition for the subject, the prediction model generating the one or more predictions based on the first and second corneal images.

20. The one or more non-transitory computer-readable media of claim 19, wherein the at least one hidden layer is configured to perform the adjustment by applying a weight associated with the first prediction to the second prediction to adjust the second prediction.

21. The one or more non-transitory computer-readable media of claim 19, wherein the at least one hidden layer is configured to perform the adjustment by adjusting the second prediction based on the first prediction indicating that the corneal condition is present in an eye of the subject.

22. The one or more non-transitory computer-readable media of claim 19, wherein the at least one input layer is configured to take, as associated inputs, the corneal images and one or more thickness maps, and wherein the prediction model is configured to generate the first and second predictions based on the corneal images and the one or more thickness maps.

23. The one or more non-transitory computer-readable media of claim 19, wherein the operations further comprise:
providing multiple frames of a same image cut from a corneal scan to the prediction model to train the prediction model, the prediction model generating at least one prediction related to presence of at least one corneal condition based on the multiple frames of the same image cut.

24. The one or more non-transitory computer-readable media of claim 23, wherein providing the multiple frames comprises providing multiple raw frames of the same image cut from the corneal scan to the prediction model such that each frame of the multiple raw frames of the same image cut comprises different noise patterns from other frames of the multiple raw frames.

25. The one or more non-transitory computer-readable media of claim 19, wherein the operations further comprise:
providing multiple raw frames of a first image cut from a first corneal scan and multiple raw frames of a second image cut from a second corneal scan to the prediction model to obtain the one or more predictions,
wherein the prediction model generates the one or more predictions based on the multiple raw frames of the first and second image cuts.

26. The one or more non-transitory computer-readable media of claim 19, wherein the one or more predictions relate to presence of at least one of corneal ectasia, Keratoconus, corneal graft rejection episode and failure, dry eye syndrome (DES), Fuchs' dystrophy, corneal limbal stem cell deficiency, cataract, or glaucoma.

27. The one or more non-transitory computer-readable media of claim 19, wherein the one or more predictions relate to presence of two or more of corneal ectasia, Keratoconus, corneal graft rejection episode and failure, dry eye syndrome (DES), Fuchs' dystrophy, corneal limbal stem cell deficiency, cataract, or glaucoma.

28. The one or more non-transitory computer-readable media of claim 19, wherein the prediction model comprises a neural network.

* * * * *